United States Patent
Erfle et al.

(10) Patent No.: US 7,049,145 B2
(45) Date of Patent: May 23, 2006

(54) VACCINIA VIRUS MVA-E3L-KNOCKOUT-MUTANTS AND USE THEREOF

(75) Inventors: Volker Erfle, München (DE); Simone Hornemann, München (DE); Gerd Sutter, München (DE)

(73) Assignee: GSF-Forschungszentrum fur Umwelt und Gesundheit, GmbH, Munich (DE)

( * ) Notice: Subject to any disclaimer, the term of this patent is extended or adjusted under 35 U.S.C. 154(b) by 0 days.

(21) Appl. No.: 10/488,987

(22) PCT Filed: Sep. 11, 2002

(86) PCT No.: PCT/EP02/10199

§ 371 (c)(1),
(2), (4) Date: Aug. 6, 2004

(87) PCT Pub. No.: WO03/023040

PCT Pub. Date: Mar. 20, 2003

(65) Prior Publication Data

US 2005/0028226 A1 Feb. 3, 2005

(30) Foreign Application Priority Data

Sep. 11, 2001 (DE) ................. 101 44 664

(51) Int. Cl.
*C12N 15/863* (2006.01)
*C12N 7/00* (2006.01)
*C12N 7/01* (2006.01)

(52) U.S. Cl. ................ 435/477; 435/235.1; 435/239; 435/320.1; 435/471

(58) Field of Classification Search ............ 435/235.1, 435/320.2, 325, 239, 471, 477, 320.1; 536/23.72
See application file for complete search history.

(56) References Cited

U.S. PATENT DOCUMENTS 5,185,146 A * 2/1993 Altenburger ............ 424/199.1
5,990,091 A * 11/1999 Tartaglia et al. ............ 514/44
6,287,570 B1 * 9/2001 Foley ................ 424/199.1

FOREIGN PATENT DOCUMENTS

| WO | WO 97/02355 | * 1/1997 |
| WO | WO 98/40500 | 9/1998 |
| WO | WO 00/73487 | 12/2000 |

OTHER PUBLICATIONS

Shors et al. Virology 227: 77-87, 1997.*
Rogan et al, Virus Genes 21:3, 193-195, 2000.*
Beattie et al., "Host-Range Restriction of Vaccinia Virus E3L-Specific Deletion Mutants," *Virus Genes*, vol. 12, No. 1, pp. 89-94, 1996.
Carroll et al., "Host Range and Cytopathogenicity of Highly Attenuated MVA Strain of Vaccinia Virus: Propagation and Generation of Recombinant Viruses in a Nonhuman Mammalian Cell Line," *Virology*, vol. 238, No. 2, pp. 198-211, Nov. 24, 1997.
Chang et al., "The E3L gene of vaccinia virus encodes an inhibitor of the intereron-induced, double-stranded RNA-dependent protein kinase," *Proc. Natl. Acad. Sci. USA*, vol. 89, pp. 4825-4829, Jun. 1992.
Chang et al., "Rescue of Vaccinia Virus Lacking the E3L Gene by Mutants of E3L," *Journal of Virology*, vol. 69, No. 10, pp. 6605-6608, Oct. 1995.

* cited by examiner

*Primary Examiner*—Mary E. Mosher
(74) *Attorney, Agent, or Firm*—Jenkins, Wilson, Taylor & Hunt, P.A.

(57) ABSTRACT

The present invention relates to mutant MVA vaccinia viruses, which are used for the generation of recombinant MVA viruses, as well as host cells, which have been infected with these mutant MVA viruses. The present invention further relates to DNA-vector constructs, and a method for the generation of recombinant MVA by using the mutant MVA viruses and the DNA-vector constructs. The mutant MVA vaccinia viruses of the present invention are characterized in that the MVA ORF 050L gene or a functional part thereof has been inactivated in the viral genome.

23 Claims, 12 Drawing Sheets

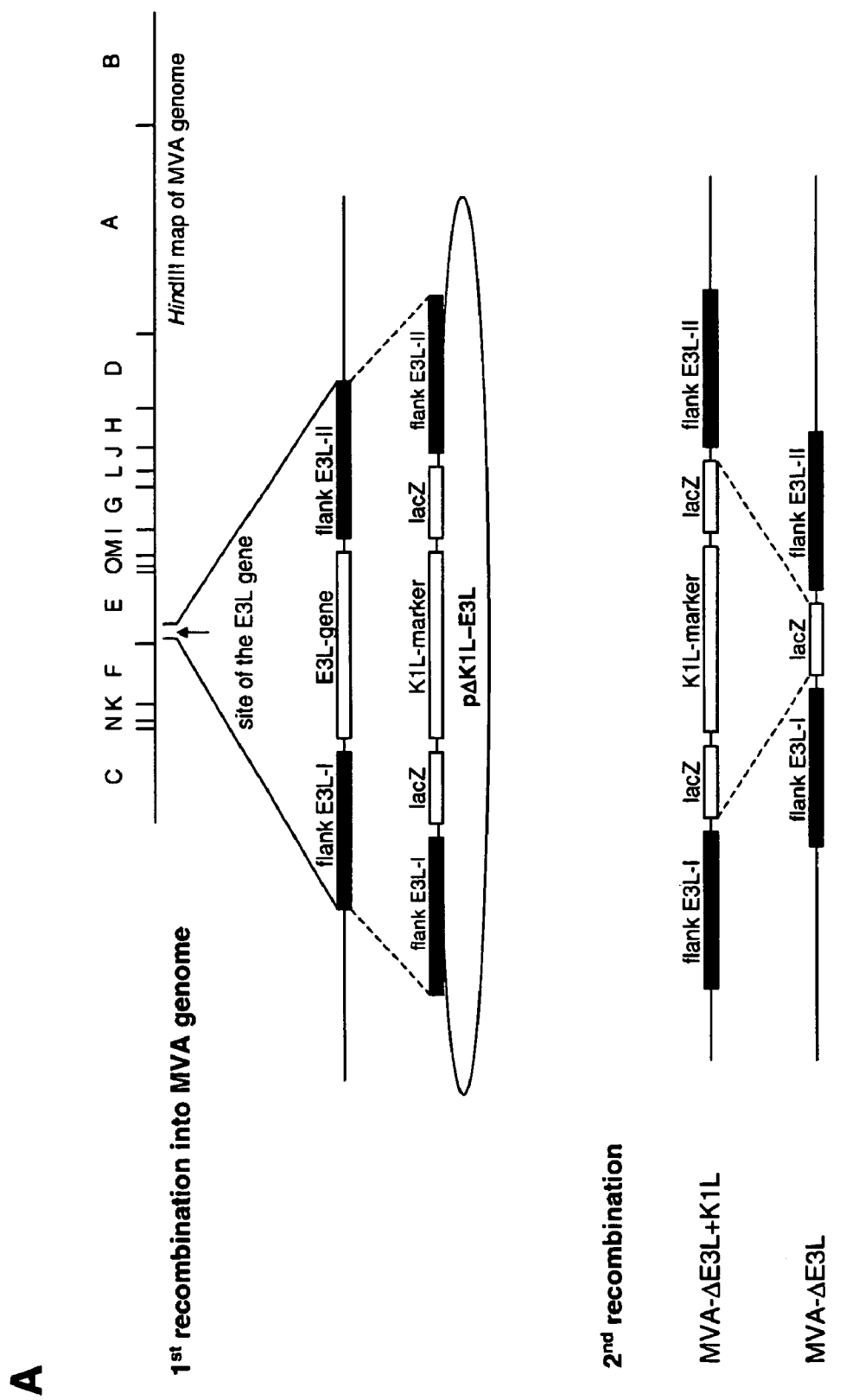

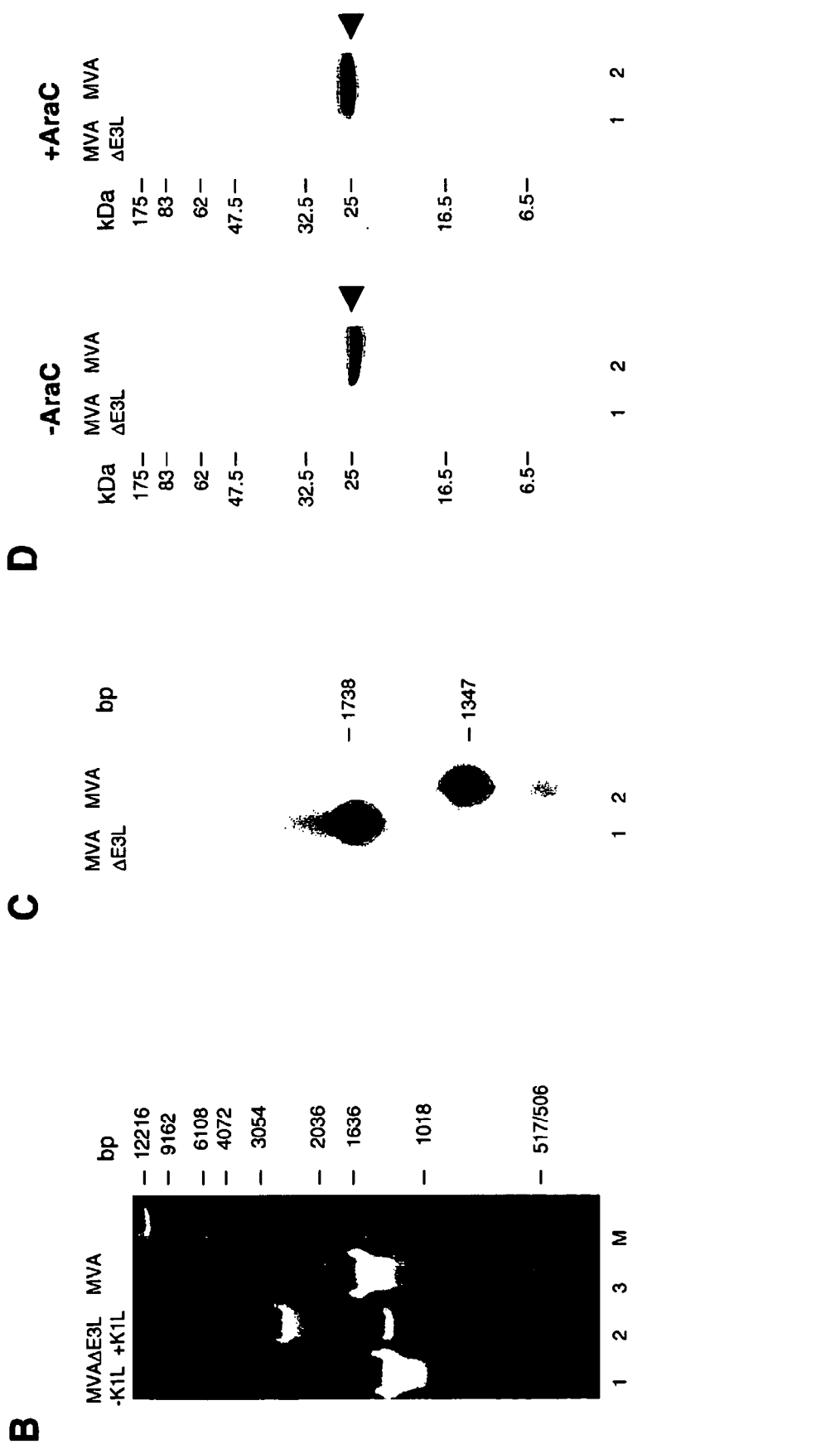

Figure 2:
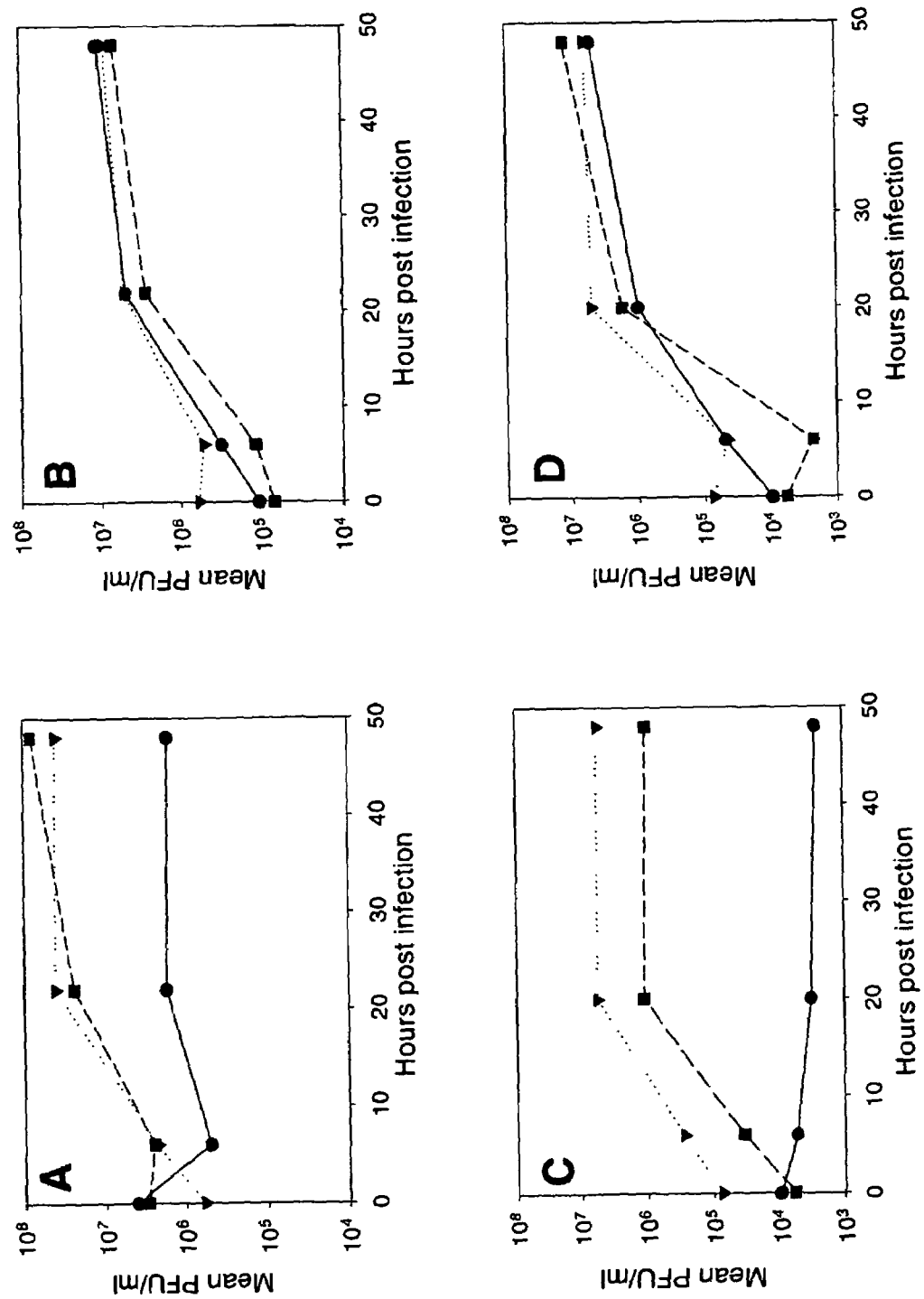

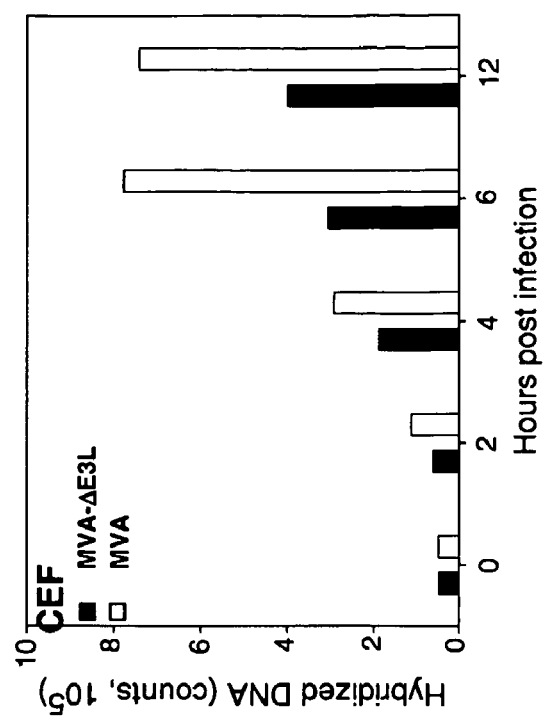
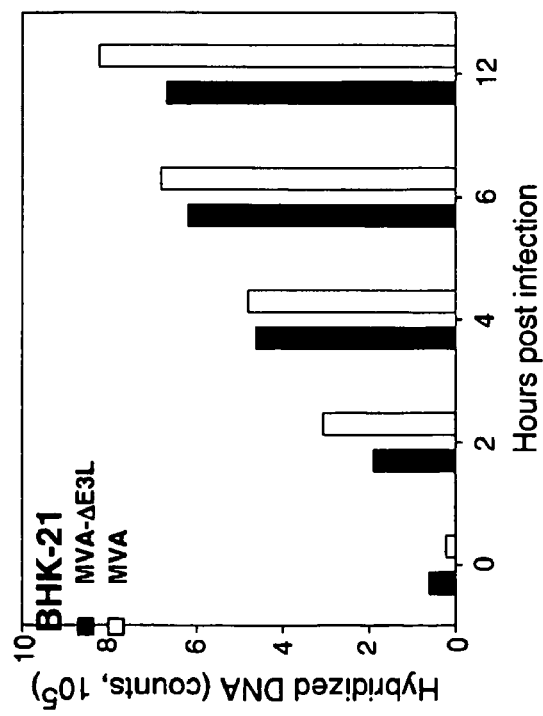

| MVA | mock |
|---|---|
| ΔE3L | E3rev |

B

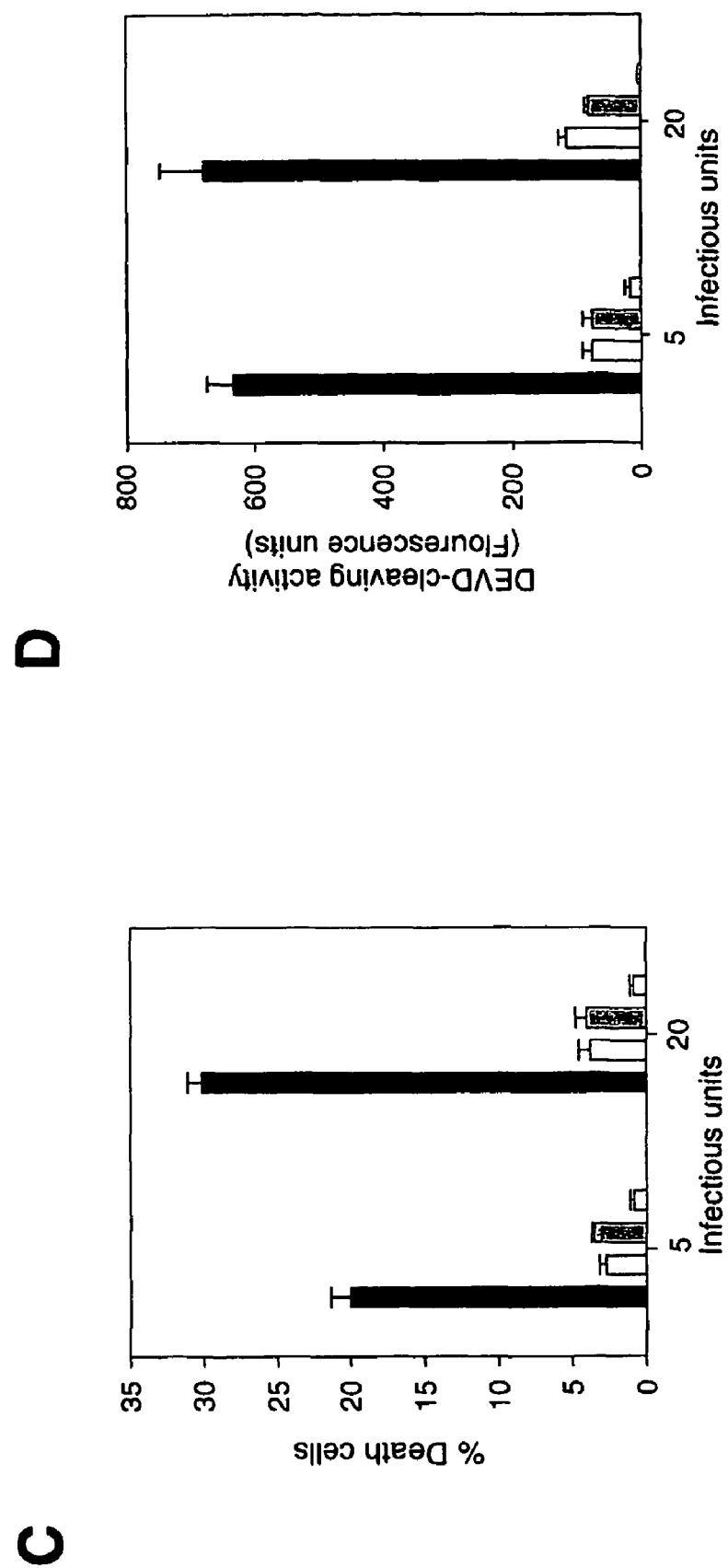

Figure 5
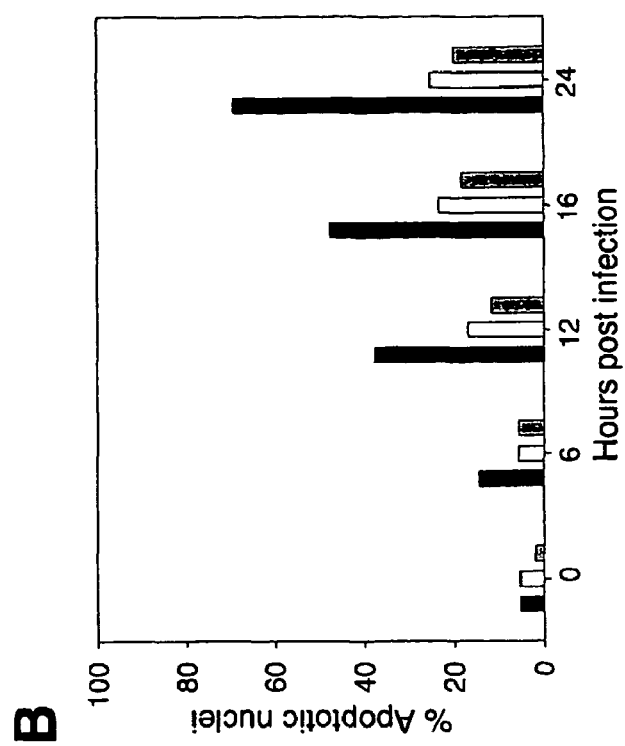
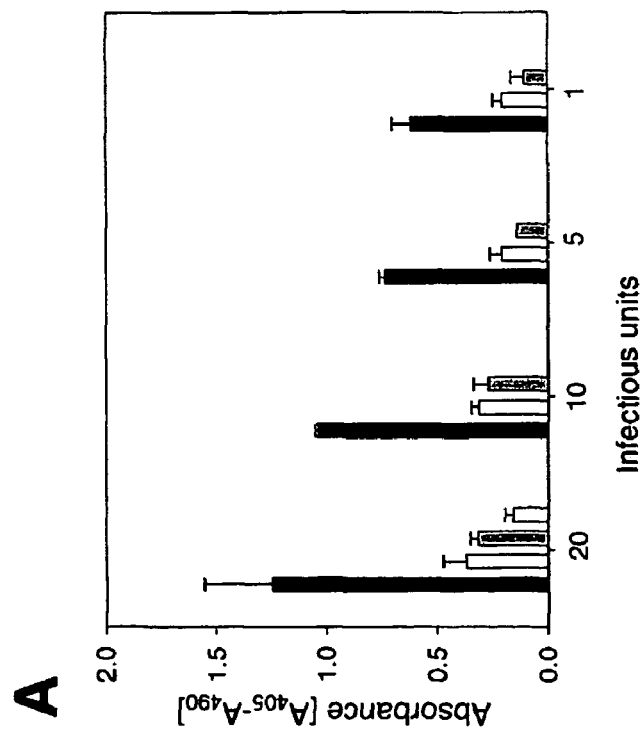

SEQUENCE LISTING

<160> NUMBER OF SEQ ID NOS: 4

<210> SEQ ID NO 1
<211> LENGTH: 39
<212> TYPE: DNA
<213> ORGANISM: Artificial
<220> FEATURE:
<223> OTHER INFORMATION: Upstream 5' primer for PCR

<400> SEQUENCE: 1
atatgattgg gcccactagc ggcaccgaaa aagaattcc                                   39

<210> SEQ ID NO 2
<211> LENGTH: 38
<212> TYPE: DNA
<213> ORGANISM: Artificial
<220> FEATURE:
<223> OTHER INFORMATION: Upstream 3' primer for PCR

<400> SEQUENCE: 2
gtcaatagcg gccgcagaca tttttagaga gaactaac                                    38

<210> SEQ ID NO 3
<211> LENGTH: 38
<212> TYPE: DNA

```
-continued
```

```
<213> ORGANISM: Artificial
<220> FEATURE:
<223> OTHER INFORMATION: Downstream 5' primer for PCR

<400> SEQUENCE: 3
tacatgaaac gcgttctatt gatgatagtg actatttc                              38

<210> SEQ ID NO 4
<211> LENGTH: 34
<212> TYPE: DNA
<213> ORGANISM: Artificial
<220> FEATURE:
<223> OTHER INFORMATION: Downstream 3' primer for PCR

<400> SEQUENCE: 4
gttacgtcgg atccagattc tgattctagt tatc                                  34
```

VACCINIA VIRUS MVA-E3L-KNOCKOUT-MUTANTS AND USE THEREOF

TECHNICAL FIELD

The present invention relates to mutant MVA vaccinia viruses, which are used for the generation of recombinant MVA viruses, as well as host cells, which have been infected with these mutant MVA viruses. The present invention further relates to DNA-vector constructs, and a method for the generation of recombinant MVA by using the mutant MVA viruses and the DNA-vector constructs.

BACKGROUND ART

Vaccinia virus belongs to the genus *Orthopoxvirus* of the family of poxviruses. Certain strains of vaccinia virus have been used for many years as live vaccine to immunize against smallpox, for example the Elstree strain of the Lister Institute in the UK. Because of the complications which may derive from the vaccination (Schär, Zeitschr. für Präventivmedizin 18, 41–44 [1973]), and since the declaration in 1980 by the WHO that smallpox had been eradicated nowadays only people at high risk are vaccinated against smallpox.

Vaccinia viruses have also been used as vectors for production and delivery of foreign antigens (Smith et al., Biotechnology and Genetic Engineering Reviews 2, 383–407 [1984]). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83, 286 and No. 110, 385). The recombinant vaccinia viruses prepared in this way can be used, on the one hand, as live vaccines for the prophylaxis of infections, on the other hand, for the preparation of heterologous proteins in eukaryotic cells.

Vaccinia virus is amongst the most extensively evaluated live vectors and has particular features in support of its use as recombinant vaccine: It is highly stable, cheap to manufacture, easy to administer, and it can accommodate large amounts of foreign DNA. It has the advantage of inducing both antibody and cytotoxic responses, and allows presentation of antigens to the immune system in a more natural way, and it was successfully used as vector vaccine protecting against infectious diseases in a broad variety of animal models. Additionally, vaccinia vectors are extremely valuable research tools to analyze structure-function relationships of recombinant proteins, determine targets of humoral and cell-mediated immune responses, and investigate the type of immune defense needed to protect against a specific disease.

However, vaccinia virus is infectious for humans and its use as expression vector in the laboratory has been affected by safety concerns and regulations. Furthermore, possible future applications of recombinant vaccinia virus e.g. to generate recombinant proteins or recombinant viral particles for novel therapeutic or prophylactic approaches in humans, are hindered by the productive replication of the recombinant vaccinia vector. Most of the recombinant vaccinia viruses described in the literature are based on the Western Reserve (WR) strain of vaccinia virus. On the other hand, it is known that this strain is highly neurovirulent and is thus poorly suited for use in humans and animals (Morita et al., Vaccine 5, 65–70 [1987]).

Concerns with the safety of standard strains of VV have been addressed by the development of vaccinia vectors from highly attenuated virus strains which are characterized by their restricted replicative capacity in vitro and their avirulence in vivo. Strains of viruses specially cultured to avoid undesired side effects have been known for a long time. Thus, it has been possible, by long-term serial passages of the Ankara strain of vaccinia virus (CVA) on chicken embryo fibroblasts, to culture a modified vaccinia virus Ankara (MVA) (for review see Mayr, A., Hochstein-Mintzel, V. and Stickl, H. (1975) Infection 3, 6–14; Swiss Patent No. 568 392). The MVA virus was deposited in compliance with the requirements of the Budapest Treaty at CNCM (Institut Pasteur, Collectione Nationale de Cultures de Microorganisms, 25, rue de Docteur Roux, 75724 Paris Cedex 15) on Dec. 15, 1987 under Depositary No. I-721.

The MVA virus has been analysed to determine alterations in the genome relative to the wild type CVA strain. Six major deletions (deletion I, II, III, IV, V, and VI) have been identified (Meyer, H., Sutter, G. and Mayr A. (1991) J. Gen. Virol. 72, 1031–1038). This modified vaccinia virus Ankara has only low virulence, that is to say it is followed by no side effects when used for vaccination. Hence it is particularly suitable for the initial vaccination of immunocompromised subjects. The excellent properties of the MVA strain have been demonstrated in a number of clinical trials (Mayr et al., Zbl. Bakt. Hyg. I, Abt. Org. B 167, 375–390 [1987], Stickl et al., Dtsch. med. Wschr. 99, 2386–2392 [1974]).

Recently, a novel vaccinia vector system was established on the basis of the host range restricted and highly attenuated MVA virus, having foreign DNA sequences inserted at the site of deletion III within the MVA genome or within the TK gene (Sutter, G. and Moss, B. (1995) Dev. Biol. Stand. Basel, Karger 84, 195–200 and U.S. Pat. No. 5,185,146). Derived by longterm serial passage in chicken embryo fibroblasts (CEF), MVA can be propagated very efficiently in CEF, but it lost its capacity to grow productively in human and most other mammalian cells (Meyer, H., Sutter, G. and Mayr A. (1991) J. Gen. Virol. 72, 1031–1038 and Sutter et al., J. Virol., Vol. 68, No. 7, 4109–4116 (1994)). Viral replication in human cells is blocked late in infection preventing the assembly to mature infectious virions. Nevertheless, MVA is able to express viral and recombinant genes at high levels even in non-permissive cells and can serve as an efficient and exceptionally safe expression vector (Sutter, G. and Moss, B. (1992) Proc. Natl. Acad. Sci. USA 89, 10847–10851).

In animal models candidate vaccines on the basis of recombinant MVA have been found immunogenic and/or protective against a variety of infectious agents including influenzavirus, immunodeficiency viruses, and *plasmodium* parasites. Moreover, the potential usefulness of recombinant MVA for therapy of cancer has been established in several tumor model systems (Moss et al. 1996, Adv Exp Med Biol 397:7; Drexler et al. 1999, Cancer Res 59:4955). Interestingly, recombinant MVA vaccines induced equal or better immune responses to target antigens and were considerably less affected by preexisting vaccinia virus-specific immunity when compared to replication competent vaccina virus vectors (Ramirez et al. 2000, J. Virol 74:7651). Currently, MVA can be considered as the vaccinia virus strain of choice for vector development. Several recombinant MVA vaccines are already under clinical investigation in tumor immunotherapy and prophylaxis of human immunodeficiency virus infection.

The MVA genome contains several open reading frames (ORFs) coding for viral regulatory factors (Antoine et al. 1998, Virology 244:365). One of them is MVA ORF 050L (Antoine et al. 1998, Virology 244:365) also known as VV gene E3L (Goebel et al. 1990, Virology 179:247). The viral protein E3L is one of the key interferon (IFN) resistance factors encoded by VV (Smith et al. 1998, Sem. Virol. 8:409). It has been shown to bind dsRNA and inhibiting the activation of both PKR and 2'-5' oligoadenylate synthetase (2-5A-S) (Chang et al. 1992, PNAS 89:4825; Rivas et al. 1998, Virology 243:406). E3L production has been described to be essential for VV replication in a range of mammalian host cells including human HeLa cells, but was found nonessential for virus propagation in CEF (Beattie et al. 1996, Virus Genes 12:89, Chang et al. 1995, J. Virol. 69:6605).

To further exploit the use of MVA, a novel way for the generation of recombinant MVA by introducing foreign genes by DNA recombination into the MVA strain of vaccinia virus has been sought. To generate recombinant MVA previously established strategies are based on the genomic co-insertion of selectable and non-selectable marker genes, e.g. the E. coli gpt and lacZ, or vaccinia virus K1L gene sequences (Sutter, G. and Moss, B. 1992, Proc. Natl. Acad. Sci. USA 89, 10847–10851; Staib, C. et al. 2000, Biotechniques, 28:1137–1148). The introduction of these heterologous markers into the MVA genome significantly improves the isolation of cloned recombinant viruses. However, during the cloning procedure there is need for supplementation of selective or chromogenic agents, such as mutagenic agent mycophenolic acid or X-Gal/DMFA, and/or the requirement for selective host cells. Furthermore, the maintenance of additional foreign gene sequences is not desireable for vector viruses to be used in clinical applications, and further genetical engineering of the viral genome is necessary to remove unwanted markers (Drexler et al. 1999, Cancer Res 59:4955; Staib, C. et al. 2000, Biotechniques, 28:1137–1148).

SUMMARY OF THE INVENTION

Therefore, it is the object of the present invention, to avoid the above-mentioned disadvantages and to provide an improved method for the generation of recombinant MVA. Since the intention was not to alter the genome of the MVA virus, it was necessary to use a method which complied with this requirement.

This is accomplished by the features of the independent claims. Preferred embodiments of the, present invention are set forth in the dependent claims.

According to the present invention, a new MVA-Knock-out mutant is provided, which is characterized in that the MVA ORF 050L gene or functional parts thereof have been inactivated in the viral genome.

Functional parts of the ORF 050L include e.g. the coding sequences for the carboxyterminal dsRNA binding domain of the E3L protein (Chang & Jacobs 1993, Virology 194: 537) or the amino-terminal domain of the E3L protein which shares sequence similarities with cellular interferon response proteins, can bind Z-DNA, and is required for E3L function in vivo (Brandt & Jacobs 2001, J. Virol. 75:850). Thus, a functional part of ORF 050L as used herein is defined as a fragment of the E3L protein, the inactivation of which in the MVA genome is leading to a lack of replication of the mutated MVA in CEF cells.

According to a preferred embodiment, the MVA ORF 050L gene or a functional part thereof has been inactivated by deletion from the viral genome.

Alternatively, a recombinant MVA defective in E3L function may be generated by sequence mutagenesis, e.g. insertional mutagenesis, leading to the inactivation of functional E3L protein synthesis by frame-shift-introduction or through specific inhibition of E3L gene transcription. This recombinant MVA can advantageously be used in a method for the introduction of foreign genes and subsequent selection of transfected strains, i.e. in a method for the generation of recombinant MVA.

Using recently established methodology of transient host range selection by consecutive cloning of engineered viruses in rabbit RK-13 and hamster BHK-21 cells (Staib et al. 2000, Biotechniques 28:1137) mutant MVA were generated having E3L coding sequences deleted from the viral genome (MVA-$_\Delta$E3L). Western blot analysis of viral proteins made during infection of BHK-21 cells showed that the viruses were unable to produce E3L protein. When compared for growth capacity in BHK-21 cells MVA-$_\Delta$E3L replicated as efficiently as original nonmutated MVA F6 (FIG. 2D).

Surprisingly, when the inventors tested virus growth in CEF, the preferred cell culture system for MVA propagation, MVA-$_\Delta$E3L was found unable to productively replicate (FIG. 2). This finding was especially surprising as deletion of E3L from VV genomes earlier was described as not affecting virus replication in CEF (Beattie et al. 1996, Virus Genes 12:89; Chang et al. 1995, J. Virol. 69:6605).

Precise reinsertion of the E3L coding sequence into the genome of MVA-$_\Delta$E3L rescued the growth capacity of the virus on CEF resulting in revertant viruses MVA-$_\Delta$E3L-Rev (FIG. 2C, 2D). This data confirmed that E3L function was essential to allow for formation of MVA progeny in CEF. Moreover, the cloning of E3L gene sequences into MVA plasmid vectors and transfection of the latter into MVA-$_\Delta$E3L-infected BHK-21 cells generated recombinant MVA which could be directly isolated by growth selection on CEF.

Starting from this surprising finding, a method has been developed, in which the MVA-$_\Delta$E3L mutant virus serves as essential tool to quickly and efficiently produce recombinant MVA for use as expression vector or vaccine.

Particular advantages are that this stringent growth selection of recombinant MVA (i) can be performed on CEF—a well established tissue culture suitable to produce MVA vaccines for clinical use, and (ii) is based on simple restoration of the original already well characterized MVA genotype.

The principle underlying the invention is that as long as MVA is present on CEF without the appropriate DNA sequences having been introduced (E3L coding sequences and optionally further DNA sequences, which are, e.g. coding for heterologous proteins), a replication does not occur. Therefore, the present method/MVA knock-out mutant is suitable for the selection of recombinant MVA and therefore serves as a tool for the effective generation of recombinant MVA.

As used herein, the term "recombinant MVA" means those MVA, which have been genetically altered, e.g. by DNA recombination techniques and which are provided for the use as a vaccine or as an expression vector.

According to the present invention, the recombinant MVA vaccinia viruses can be prepared as follows:

A DNA-construct which contains a DNA-sequence which codes for E3L protein or an E3L-derived polypeptide and a DNA sequence encoding a foreign polypeptide both flanked by DNA sequences flanking a non-essential site, e.g. a naturally occuring deletion, e.g. deletion III, within the MVA genome, is introduced into cells, preferably eucaryotic cells. Preferred eucaryotic cells are BHK-21 (ATCC CCL-10), BSC-1 (ATCC CCL-26), CV-1 (ECACC 87032605) or MA104 (ECACC 85102918) cells) productively infected with MVA-$_\Delta$E3L, to allow homologous recombination. Once the DNA-construct has been introduced into the eukaryotic cell and the E3L coding DNA and foreign DNA has recombined with the viral DNA, it is possible to isolate the desired recombinant vaccinia virus MVA upon passage in cells that require E3L function to support virus growth, e.g. CEF cells. The cloning of the recombinant viruses is possible in a manner known as plaque purification (compare Nakano et al., Proc. Natl. Acad. Sci. USA 79, 1593–1596 [1982], Franke et al., Mol. Cell. Biol. 1918–1924 [1985], Chakrabarti et al., Mol. Cell. Biol. 3403–3409 [1985], Fathi et al., Virology 97–105 [1986]).

The DNA-construct to be inserted can be linear or circular. A circular DNA is preferably used. It is particularly preferable to use a plasmid.

The DNA-construct may contain sequences flanking the left and the right side of a non-essential site, e.g. the site of deletion III, within the MVA genome (Sutter, G. and Moss, B. (1992) Proc. Natl. Acad. Sci. USA 89, 10847–10851).

The foreign DNA sequence may be inserted between the sequences flanking the non-essential site, e.g. the naturally occuring deletion.

The foreign DNA sequence can be a gene coding for a therapeutic polypeptide, e.g. t-PA or interferon, or from a pathogenic agent. Pathogenic agents are to be understood to be viruses, bacteria and parasites which may cause a disease, as well as tumor cells which multiply unrestrictedly in an organism and may thus lead to pathological growths. Examples of such pathogenic agents are described in Davis, B. D. et al., (Microbiology, 3rd ed., Harper International Edition). Preferred genes of pathogenic agents are those of influenza viruses, of measles and respiratory syncytial viruses, of dengue viruses, of human immunodeficiency viruses, for example HIV I and HIV II, of human hepatitis viruses, e.g. HCV and HBV, of herpes viruses, of papilloma viruses, of the malaria parasite *Plasmodium falciparum*, and of the tuberculosis-causing *Mycobacteria*.

Preferred genes encoding tumor associated antigens are those of melanoma-associated differentiation antigens, e.g. tyrosinase, tyrosinase-related proteins 1 and 2, of cancer testes antigens, e.g. MAGE-1,-2,-3, and BAGE, of non-mutated shared antigens overexpressed on tumors, e.g. Her-2/neu, MUC-1, and p53.

In order for it to be possible for the foreign DNA sequence or the gene to be expressed, it is necessary for regulatory sequences, which are required for the transcription of the gene, to be present on the DNA. Such regulatory sequences (called promoters) are known to those skilled in the art, for example those of the vaccinia 11 kDa gene as are described in EP-A-198, 328, and those of the 7.5 kDa gene (EP-A-110, 385).

The DNA-construct can be introduced into the cells by transfection, for example by means of calcium phospate precipitation (Graham et al., Virol. 52, 456–467 [1973]; Wigler et al., Cell 777–785 [1979] by means of electroporation (Neumann et al., EMBO J. 1, 841–845 [1982]), by microinjection (Graessmann et al., Meth. Enzymology 101, 482–492 (1983)), by means of liposomes (Straubinger et al., Methods in Enzymology 101, 512–527 (1983)), by means of spheroplasts (Schaffher, Proc. Natl. Acad. Sci. USA 77, 2163–2167 (1980)) or by other methods known to those skilled in the art. Transfection by means of calcium phosphate precipitation is preferably used.

To prepare vaccines, the MVA vaccinia viruses generated according to the invention are converted into a physiologically acceptable form. This can be done based on the many years of experience in the preparation of vaccines used for vaccination against smallpox (Kaplan, Br. Med. Bull. 25, 131–135 [1969]). Typically, about $10^6$–$10^7$ particles of the recombinant MVA are freeze-dried in 100 ml of phosphate-buffered saline (PBS) in the presence of 2% peptone and 1% human albumin in an ampoule, preferably a glass ampoule. The lyophilisate can contain extenders (such as mannitol, dextran, sugar, glycine, lactose or polyvinylpyrrolidone) or other aids (such as antioxidants, stabilizers, etc.) suitable for parenteral administration. The glass ampoule is then sealed and can be stored, preferably at temperatures below −20° C., for several months.

For vaccination the lyophilisate can be dissolved in 0.1 to 0.2 ml of aqueous solution, preferably physiological saline, and administered parenterally, for example by intradermal inoculation. The vaccine according to the inverition is preferably injected intracutaneously. Slight swelling and redness, sometimes also itching, may be found at the injection site (Stickl et al., supra). The mode of administration, the dose and the number of administrations can be optimized by those skilled in the art in a known manner. It is expedient where appropriate to administer the vaccine several times over a lengthy period in order to obtain a high level immune responses against the foreign antigen.

As a summary, the method of the present invention for the generation of recombinant MVA comprises the following steps: Infecting the host cells as described above with the recombinant MVA, transfecting the host cells with a DNA-vector construct of the present invention and selecting restored MVA by growth on CEF cells or chicken embryo derived LSCC-H32 cells (Roth & Kaaden 1985 Appl Environ Microbiol 49:634–636) or avian cells (e.g. quail fibroblasts QT6 or QT35 cells).

BRIEF DESCRIPTION OF THE DRAWINGS

FIG. 1

Construction and characterization of MVA-$_\Delta$E3L. (A) Schematic maps of the MVA genome and the plasmid p$_\Delta$K1L-E3L designed for the deletion of the E3L gene sequences. The $_{Hin}$dIII restriction endonuclease sites of the MVA genome are indicated on the top. MVA-DNA sequences adjacent to the E3L gene (flank-E3LI and flank-E3LII) were cloned into p$_\Delta$K1L to direct insertion of the K1L selectable marker by homologous recombination resultig in the deletion of the E3L open reading frame (ORF) from the MVA genome. K1L gene expression allows selective growth of the instable intermediate virus MVA-$_\Delta$E3L+K1L in RK13-cells. The final mutant virus MVA-$_\Delta$E3L results after deletion of the K1L marker gene during a second homologous recombination involving additional repetitive sequences (LacZ). (B) PCR analysis of viral DNA. (C) Southern blot analysis of viral DNA. (D) Western blot analysis of lysates from CEF infected with MVA-$_\Delta$E3L or MVA in the presence or absence of AraC. The E3L protein band detected by the E3L-specific mouse monoclonal antibody TW9 is marked by an arrowhead.

FIG. 2:

Analysis of virus growth in CEF(A, C) and BHK (B, D) cells after high (A,B) or low (C,D) dose infection with MVA-$_\Delta$E3L (●), MVA$_{wt}$ (MVA-F6) (■) and MVA-E3rev ▼). FIG. 2C shows the multiple-step growth of MVA-$_\Delta$E3L in comparison to MVA-E3rev and wildtype MVA in CEF cells. FIG. 2D shows the multiple-step growth of MVA-$_\Delta$E3L in comparison to MVA-E3rev and wildtype MVA in BHK cells.

FIG. 3:

Viral polypeptide synthesis. (A) BHK and (B) CEF cells were infected with MVA-$_\Delta$E3L, MVA or MVA-E3rev (lanes 9–12) and labeled with [$^{35}$S]methionine for 30 min at the indicated hour post infection (hpi). Cell lysates were analyzed by gel electrophoresis on a 10% polyacrylamide gel and visualized by autoradiography. Protein standards (lane M) are indicated by their molecular masses (in kilo Daltons) on the left. Uninfected cells (U) served as control. Viral DNA synthesis (C, D). DNA isolated from BHK-21 (C) or CEF (D) at 0 h, 2 h, 4 h, 6 h and 8 h after infection with MVA-$_\Delta$E3L or MVA was immobilized on a Hybond N$_+$ membrane and analyzed by hybridization of a $^{32}$P-labeled MVA-DNA probe. Radioactivity was quantitated with a phophorimager analyzer.

FIG. 4:

Induction of apoptosis by MVA-$_\Delta$E3L in CEF cells. (A) Semiconfluent monolayers of CEF cells were either non-infected (lane 7) or infected with MVA-$_\Delta$E3L (lanes 1, 2), $_{wt}$MVA (lanes 3, 4) or MVA-E3rev (lanes 5, 6) with an MOI of 20 PFU/cell for DNA fragmentation analysis. Viral DNA extracts were obtained 16 h post infection (lanes 1, 3, 5) and 24 h post infection (lanes 2, 4, 6), separated by gel electrophoresis through 1% agarose, and visualized by ethidium bromide staining. As a positive control a sample from a DNA-Laddering kit (Roche Diagnostics) was applied (lane 8). (B) The Hoechst 3343 staining was performed with mock-infected or MVA-infected CEF cells grown on coverslips. After 16 h the cells were stained for 30 min with Hoechst 3343. Micrographs were taken for CEF cells either mock infected (mock) or infected with MVA-$_\Delta$E3L ($_\Delta$E3L), non-recombinant MVA (MVA) or MVA-E3rev (E3rev) at an MOI of 5 PFU/cell. (C) Apoptotic cells stained with Hoechst 3343 were counted in CEF cells infected with MVA-$_\Delta$E3L (■, 1$^{st}$ position), MVA (■, 2$^{nd}$ position) or MVA-E3rev (■, 3$^{rd}$ position) at an MOI of 5 and 20 PFU/cell 16 and 24 h after infection. Results are given as the mean/3× the SEM. Mock-infected CEF are indicated in light grey, 4$^{th}$ position. (D) Induction of DEVD-cleaving was measured in either uninfected CEF cells or in cells infected with an MOI of 5 and 20 PFU/cell of MVA-$_\Delta$E3L (■), MVA (■) and MVA-E3rev (■). DEVD-cleaving activity was measured in triplicates of 10 $\mu$l from each mixture as described in materials and methods. Results are given as the mean/3× the SEM.

FIG. 5:

Dosis- and time-dependent extent of apoptosis. (A) The extent of apoptosis depending on the infectious dosis was measured by ELISA either in mock-infected CEF (light grey, 4$^{th}$ position) or in cells infected with MVA-$_\Delta$E3L (■, 1$^{st}$ position), MVA (■, 2$^{nd}$ position) and MVA-E3rev (■, 3$^{rd}$ position). The cell death detection ELISA was performed according to the manufacturers instructions 16 h post infection (Roche Diagnostics). Absorbance at 405 nm (Reference: 490 nm) was measured. Results are given as the mean/2× the SEM. (B) The time-dependent extent of apoptosis was analyzed in CEF cells either mock-infected or infected with MVA-$_\Delta$E3L (■), MVA (■) or MVA-E3rev (■) at an MOI of 20 PFU/cell. Cells were harvested at indicated time points, fixed over night, stained with propidium iodide, and analyzed by flow cytometry.

FIG. 6

Synthesis of chicken IFN type I after infection of CEF with MVA-$_\Delta$E3L. CEF monolayers grown in 6-well tissue culture plates were inoculated with 10 Iu/cell of MVA-$_\Delta$E3L (C), MVA (B), MVA-E3rev (D), wild-type vaccinia virus CVA (A). Cell-free supernatants were collected at 24 h after infection and tested for activities of chicken IFN type I in comparison to recombinant chicken IFN (recIFN, 250 U/ml).

FIG. 7

Effect of IFN treatment on MVA infection in CEF. CEF monolayers were incubated with increasing amounts of recombinant chicken IFN type I for 24 h, before infecting the cultures at low MOI with MVA, MVA-$_\Delta$E3L, or MVA-E3rev, or for comparison with vaccinia viruses CVA or WR. At 48 h after infection cell monolayers were fixed and foci of virus infected cells were visualized using vaccinia virus-specific immunostaining.

FIG. 8

Generation of recombinant MVA by E3L rescue and growth selection in CEF-cells. (A) Schematic maps of the MVA genome ($_{Hind}$III restriction map) and the vector plasmid pIII-E3L-P$_{mH5}$-gfp are shown. Flank-1 and flank-2 correspond to DNA sequences which target foreign genes as well as the selectable marker E3L into the site of deletion III within the MVA genome. The foreign gene is controlled by the modified vacciniavirus early/late promoter PmH5. (B) PCR analysis of viral DNA. Genomic DNA isolated from eight different clones of recombinant MVA-P$_{mH5}$-gfp (rec-MVA), or from non-recombinant MVA (WT), and plasmid pIII-E3L-P$_{mH5}$-gfp DNA served as template DNAs for the amplification of characteristic DNA fragments. A 1-kb DNA ladder was used as standard for the molecular weights of the DNA fragments.

The detailed example which follows is intended to contribute to a better understanding of the present invention. However, it is not intended to give the impression that the invention is confined to the subject-matter of the example.

DETAILED DESCRIPTION OF THE INVENTION

EXAMPLES

1. Growing and Purification of the Viruses 1.1 Growing of the MVA and the MVA-$_\Delta$E3L Virus The MVA virus is a greatly attenuated vaccinia virus produced by serial passages of the original CVA strain on chicken embryo fibroblast (CEF) cultures. For a general rewiew of the history of the production, the properties and the use of the MVA strain of vaccinia, reference may be made to the summary published by Mayr et al. in Infection 3, 6–14 [1975]. Owing to the adaptation to CEF, growth of the MVA virus on other cell systems is greatly restricted. Exceptionally, baby hamster kidney cells (BHK-21), a well characterized, easily maintained cell line, supports MVA growth and as proficient expression of recombinant genes as the highly efficient CEF and has been recommended for standardized MVA propagation during the development of expression vectors and live recombinant vaccines (Drexler et al. 1998, J. Gen. Virol., 79, 347–352).

The MVA virus was normally grown on CEF cells, the host cell for which it had been adapted. To prepare the CEF cells, 11-days old embryos were isolated from incubated chicken eggs, the extremities were removed, and the embryos were cut into small pieces and slowly dissociated in a solution composed of 25% trypsin at room temperature for 2 hours. The resulting cell suspension was diluted with one volume of medium I (MEM Eagle, for example obtainable from Gibco, Basle, Switzerland; Order No. 072-1500) containing 5% fetal calf serum (FCS), penicillin (100 units/ml), streptomycin (100 mg/ml) and 2 mM glutamine and filtered through a cell screen (for example obtainable from Technomara AG, Zurich, Switzerland, Order No. Bellco 1985, 150 mesh), and the cells were sedimented by centrifugation at 2000 rpm in a bench centrifuge (Hermle KG, D-7209 Gosheim, FRG) at room temperature for 5 minutes. The cell sediment was taken up in ¼ of the original volume of medium I, and the CEF cells obtained in this way were spread on cell culture dishes. They were left to grow in medium I in a $CO_2$ incubator at 37° C. for 1–2 days, depending on the desired cell density, and were used for infection either directly or after 1–2 further cell passages. A clear description of the preparation of primary cultures can be found in the book by R. I. Freshney, "Culture of animal cell", Alan R. Liss Verlag, New York [1983] Chapter 11, page 99 et seq.

The MVA-$_\Delta$E3L is routinely propagated in baby hamster kidney BHK-21 (American Type Culture Collection ATCC CCL-10) cells which were grown in minimal essential medium (MEM) supplemented with 10% fetal calf serum (FCS). BHK-21 cells were maintained in a humidified air–5% $CO_2$ atmosphere at 37° C.

The viruses were used for infection as follows. Cells were cultured in 175 $cm^2$ cell culture bottles. At 80–90% confluence, the medium was removed and the cells were incubated for one hour with an MVA virus suspension (0.01 infectious particles (=pfu) per cell, 0.01 ml/$cm^2$) in phosphate-buffered saline (PBS/Dulbecco, for example Animed AG, Muttenz, Switzerland, Order No. 23.100.10). Then medium was added (0.2 ml/$cm^2$) and the bottles were incubated at 37° C. for 2–3 days until about 80% of the cells had rounded. The virus lysates were stored with the cells and medium, without treatment, in the cell culture bottles at −30° C. before further processing (purification etc.)

1.2 Purification of the Viruses

The purification steps undertaken to obtain a virus preparation which was as pure as possible and free from components specific to the host cell were identical for the MVA and WR viruses (Joklik, Virology 18, 9–18 [1962], Zwartouw et al., J. gen. Microbiol. 29, 523–529 [1962]). The cell cultures which had been infected and then stored at −30° C. were thawed, the residual cells were shaken off or scraped off the plastic substrate, and cells and virus were removed from the medium by centrifugation (Sorvall centrigue, GSA rotor, 1 hour at 5000 rpm and 10° C.). The sediment, composed of viral and cell particles, was suspended once in PBS (10–20 times the volume of the sediment), and the suspension was centrifuged as above. The new sediment was suspended in 10 times the volume of RSB buffer (10 mM Tris-HCl pH 8.0, 10 mM KCl, 1 mM $MgCl_2$), and the suspension was briefly treated with ultrasound (Labsonic 1510 equipped with a 4 mm diameter tip, obtainable from Bender and Hobein, Zurich, Switzerland, 2×10 seconds at 60 watts and room temperature) in order to disintegrate remaining still intact cells and to liberate the virus particles from the cell membranes. The cell nuclei and the larger cell debris were removed in the subsequent brief centrifugation of the suspension (Sorvall GSA rotor obtainable from DuPont Co., D-6353 Bad Nauheim, FRG; 3 minutes at 3000 rpm and 10° C.). The sediment was once again suspended in RSB buffer, treated with ultrasound and centrifuged, as described above.

The collected supernatants containing the free virus particles were combined and layered over a pad composed of 10 ml of 35% sucrose in 10 mM Tris-HCl, pH 8.0, and centrifuged in a Kontron TST 28.38/17 rotor (Kontron Instrumente, Zurich, Switzerland; corresponds to a Beckman SW 27 rotor) for 90 minutes with 14,000 rpm at 10° C.). The supernatant was decanted, and the sediment containing the virus particles was taken up in 10 ml of 10 mM Tris-HCl, pH8.0, homogenized by brief treatment with ultrasound (2×10 seconds at room temperature, apparatus as described above), and applied to a stepped gradient for further purification. The steps of the gradient were each composed of 5 ml of sucrose in 10 mM Tris-HCl, pH 8.0 (sucrose concentration steps: 20%, 25%, 30%, 35% and 40%). The gradient was centrifuged in a Kontron TST 28.38/17 rotor at 14,000 rpm 10° C. for 35 minutes. After this centrifugation, several discrete zones containing virus particles were visible in the region of the gradient between 30% and 40% sucrose. This region was siphoned off from the gradient (10 ml), the sucrose solution was diluted with PBS (20 ml) and the virus particles were sedimented therefrom by centrifugation (Kontron TST 28.38/17 rotor, 90 minutes at 14,000 rpm, 10° C.). The sediment, which now consisted mostly of pure virus particles, was taken up in PBS in such a way that the virus concentrations corresponded on average to 1–5×10$^9$ pfu/ml. The purified virus stock solution was used either directly or diluted with PBS for the subsequent experiments.

2. Construction and Characterization of MVA-$_\Delta$E3L Viruses 2.1. Construction of E3L Deletion Plasmid MVA genomic DNA sequences flanking the E3L gene were amplified by polymerase chain reaction using DNA of MVA (cloned isolate F6, 582$^{nd}$ passage on CEF) as a template. The primers of the upstream flanking region of E3L were 5'-ATATGATT GGGCCCACTAGCGGCACCGAAAAAGAATTCC-3' (SEQ ID NO:1) (ApaI site underlined) and 5'-GTCAATA GCGGCCGCAGACATTTTTAGAGAGAACTAAC-3' (SEQ ID NO:2) (NotI site underlined). The primer for the downstream region were 5'-TACATGAA ACGCGTTCTATTGATGATAGTGACTATTTC-3' (SEQ ID NO:3) (MluI site underlined) and 5'-GTTACGTC GGATCCAGATTCTGATTCTAGTTATC-3' (SEQ ID NO:4) (BamHI site underlined). The constucts were cut with ApaI/NotI or MluI/BamHI and inserted into the corresponding sites of the plasmid p$_A$K1L (Staib et al. 2000, Biotechniques, 28:1137–1148) to obtain the E3L deletion plasmid p$_A$E3L-K1L 2.2. Formation and Isolation of Mutant Virus MVA-$_\Delta$E3L Mutant virus MVA-$_\Delta$E3L was generated using previously described methodology (Staib et al. 2000, Biotechniques, 28:1137–1148). Briefly, monolayers of 1×10$^6$ confluent BHK-21 cells grown in 6-well tissue-culture plates (Costar, Corning N.Y., USA) were infected with MVA at a multiplicity of infection (MOI) of 0.01 IU per cell. Ninety min after infection cells were transfected with 10 $\mu$g of plasmid p$_A$E3L-K1L DNA per well using calcium phosphate (Ce/lPhect Transfection Kit, Amersham Pharmacia Biotech, Freiburg, Germany) as recommended by the manufacturer. Forty-eight hours after infection the cells were harvested, freeze-thawed three times, and homogenized in a cup sonicator (Sonopuls HD 200, Bandelin, Germany). Ten-fold serial dilutions (10$^{-1}$ to 10$^{-4}$) of the harvested material in medium were used to infect subconfluent monolayers of RK-13 cells grown in 6-well tissue-culture plates. After three days incubation at 37° C. foci of RK-13 cells infected with mutant MVA-$_\Delta$E3L were picked in a 20 μl volume by aspiration with an air-displacement pipette, transferred to microcentrifuge tubes containing 500 μl medium, and processed by freeze-thawing and sonication for another infection of RK-13 cell monolayers. After elimination of all parental MVA during passage on RK-13 cells, ten-fold serial dilutions ($10^{-1}$ to $10^{-6}$) of the recombinant viruses were used for infection of subconfluent BHK-21 cells grown in 6-well tissue-culture plates (Costar, Corning N.Y., USA). Well separated foci of infected BHK-21 cells were harvested to isolate K1L-negative mutant MVA-$_\Delta$E3L.

Viral DNA from cloned MVA isolates was routinely analyzed by PCR as described previously (Staib et al 2000). To monitor the E3L gene locus in genomes of mutant MVA, we used oligonucleotides from gene sequences adjacent to ORF E3L: 5'-ATA TGA TTG GGC CCA CTA GCG GCA CCG AAA AAG AAT TCC-3' (SEQ ID NO:1) and 5'-TAC ATG AAA CGC GTT CTA TTG ATG ATA GTG ACT ATT TC-3' (SEQ ID NO:3).

Southern blot analysis. Total DNA isolated from virus-infected BHK cells was digested with $_{Eco}$RI, separated by gel electrophoresis in 0.8% agarose, transferred to a Hybond N+ membrane, and hybridized to a DNA probe consisting of a PCR fragment spanning the downstream flanking region of the E3L gene labeled with [$\alpha$-$^{32}$P]CTP. Prehybridization and hybridization was performed according to the QuickHyb protocol (Stratagene GmbH, Heidelberg, Germany). Membranes were washed twice with 2× sodium chloride/sodium citrate pH 7.0 solution (SSC)/0.1% SDS at 65° C. for 30 min and twice at room temperature. The blots were exposed to a Kodak x-Omat film.

Western blot analysis. Confluent BHK-21 cell monolayers grown in 6-well tissue culture plates were inoculated with 10 IU virus/cell for one hour. Infected cells were briefly washed with medium and incubated with fresh medium with and without addition of cytosine arabinoside (AraC, 40 μg/ml). After 24 h cell lysates were prepared and separated by SDS-12% polyacrylamide gel electrophoresis (PAGE). Proteins were then electroblotted onto nitrocellulose membranes (BiORad) for 2 h in a buffer containing 25 mM Tris, 19,2 mM glycine and 20% methanol (pH 8.3). After blocking overnight in blocking buffer containing 2% (w/v) BSA, 0.05% (v/v) Tween, 50 mM Tris, 150 mM NaCl, (pH 7.5), the blot was probed with 10-fold diluted supernatants from hybridoma TW2.3 producing an anti-E3L mouse monoclonal antibody (Yuwen et al. Virology 195, 732–744, 1993) in blocking buffer for 1 h. After being washed, the blot was incubated for 1 h with peroxidase-conjugated polyclonal goat anti-mouse antibody (IgG (H+L)), Cat. No. 111-035-114; Dianova, Hamburg, Germany, dilution 1:10000) diluted 5000-fold in blocking buffer, washed again, and developed by visualization with enhanced chemiluminescence procedure (ECL, manufacturer) using Kodak x-Omat film.

2.3. Analysis of Virus Growth

To determine low-multiplicity-growth profiles, virus multiplication was monitored after infecting CEF or BHK-21 monolayers with 0.05 infectious units (IU) UVA, MVA-$_\Delta$E3L or MVA-E3rev per cell. One-step-growth of MVA, MVA-$_\Delta$E3L and MVA-E3rev was analyzed infecting cells at a multiplicity of infection (MOI) of 5 IU. For all infection experiments confluent monolayers grown in 6-well tissue culture plates were used. After virus adsorption for 60 min at 37° C., the inoculum was removed. The infected cells were washed twice with RPMI 1640 and incubated with fresh RPMI 1640 medium containing 10% FCS at 37° C. in a 5% $CO_2$ atmosphere. At multiple time points post infection (p.i.) infected cells were harvested and virus was released by freeze-thawing and brief sonication. Serial dilutions of the resulting lysates were plated on confluent BHK-21 monolayers grown in 6-well plates as replicates of two. For vaccinia virus-specific immunostaining of virus infected cells, media were removed 48 hours p.i., cells were briefly fixed in acetone:methanol (1:1, 1 ml/well). After washing, and blocking in PBS-2% FCS cells were incubated for 60 min with polyclonal rabbit anti-vaccinia antibody (IgG fraction, Biogenesis Ltd, Poole, England, Cat. No. 9503-2057, diluted 1:10000 in PBS-3% FCS). After washing cells with PBS, peroxidase-conjugated polyclonal goat anti-rabbit antibody (e.g. 2nd antibody horseradish peroxidase-conjugated (IgG (H+L)), Cat. No. 111-035-114; Dianova, Hamburg, Germany, dilution 1:1000 in PBS-3% FCS) was added, and incubated for 45 min. After washing with PBS, antibody-labeled cells were developed with dianisidine (Sigma No. 09143) substrate solution, foci of stained cells were counted, and virus titers were calculated (IU/ml) as with vaccinia virus plaque assay.

Analysis of viral DNA. Genomic viral DNA was isolated from infected cells as described previously (Earl P & Moss B, Current Protocols in Molecular Biology). To assess viral DNA replication total DNA was transferred with a slot blot apparatus to Hybond N+ membranes and hybridized to a $^{32}$P-labeled MVA DNA probe. Radioactivity was quantitated with a phosporimager analyser (BiORad).

Analysis of [$^{35}$S]methionine-labeled polypeptides. BHK and CEF cell monolayers, in 12-well plates, were either mock infected or infected with UVA, MVA-$_\Delta$E3L or MVA-E3rev at an MOI of 20. Following 45 min adsorption at 4° C., virus inocula were replaced by pre-warmed tissue culture medium and incubated at 37° C. in a 5% $CO_2$ atmosphere. At indicated time points post-infection, cells were washed with methionine-free medium at 37° C. for 10 min, and 50 μCi of [$^{35}$S]methionine were added to each well and incubated for 30 min at 37° C. Cytoplasmic extracts of infected cell monolayers were prepared by adding 0.2 ml 0.5% Nonidet P-40 lysis buffer (20 mM Tris-HCL, 10 mM NaCl (pH 8.0)) for 10 min. Polypeptides from cell extracts were separated by 10% sodium dodecyl sulfate (SDS) polyacrylamide gel electrophoresis (PAGE) and analyzed by autoradiography.

Analysis of DNA fragmentation. CEF were mock-infected or infected with MVA, MVA-$_\Delta$E3L and MVA-E3rev at an MOI of 20. Cells were harvested at 16 h and 24 h p.i. and total DNA was extracted as described. Precipitated DNA was resuspended in 100 μl $H_2O$, treated with RNase (final concentration: 1 mg/ml) for 15 min at 37° C. and resolved in an 1% agarose gel. DNA fragments were visualized by staining with ethidium bromide.

Hoechst Staining. CEF cells grown to confluency in a 12-well plates containing Ø 12 mm glass coverslips were either non-infected or infected with MVA, MVA-$_\Delta$E3L or MVA-E3rev at MOIs of 5 or 20. Cells were stained at 16 or 24 h p.i. with Hoechst 3343 for 30 min at room temperature and photographed under a fluorescence microscope. The ratio of apoptotic cells to non-apoptotic cells was determined by counting and presented as the mean and three times the standard error of the mean (mean/3× the SEM).

Assay for caspase activity. Monolayers of $5\times10^5$ confluent CEF grown in 12-well tissue-culture plates were either mock-infected or infected with MVA, MVA-$_\Delta$E3L and MVA-E3rev at an MOI of 20. Ninety minutes after infection at 4° C., cells were washed twice with MEM containing 10% lactalbumin and 5% BMS and incubated for 16 h at 37° C. Cells were harvested, collected by centrifugation, washed once in PBS, and lysed by incubating $2 \times 10^7$ cells/ml in lysis buffer (1% Nonidet P-40, 50 mM Tris-HCl, 150 mM NaCl, (pH 8.0)) for 10 min on ice followed by vigorous vortexing. Extracts were cleared by centrifugation for 5 min at 10.000×g at 4° C. and transferred to fresh vials. To determine DEVD-cleaving activity, extracts were diluted 1:10 in reaction buffer (mitotic dilution buffer (Lazebnik, Y. A., Cole, S., Cooke, C. A., Nelson, W. G. and Earnshaw, W. C. (1993). Nuclear events of apoptosis in vitro cell free mitotic extracts: a model system for analysis of the active phase of apoptosis. J. Cell. Biol. 123: 7–22) containing 10 mM HEPES-KOH, 40 mM β-glycerophosphate, 50 mM NaCl, 2 mM MgCl; 5 mM EGTA, and 1 mM dithiothreitol [DTT], (pH 7.0) supplemented with 0.1% CHAPS {3'-[(3'-cholamidopropyl)-dimethylammonio]-1-propanesulfonate}, 100 µg of bovine serum albumin and acetyl-DEVD-7-amino-4-methylcoumarib (DEVD-AMC) (final concentration: 10 µM). Reactions were performed in triplicate in flat-bottomed 96-well pates at 37° C. for 1 h. Free AMC was then measured by determining the fluorescence at 390 nm (excitation) and at 460 nm (emission) in a Millipore Cytofluor 96 reader. Values were calculated by subtracting the background fluorescence (buffer and substrate alone) and are presented as the mean and three times standard error of the mean (mean/3× the SEM).

Measurement of apoptosis by ELISA. Confluent CEF monolayer with $1 \times 10^5$ cells were mock infected or infected with MVA, MVA-$_\Delta$E3L and MVA-E3rev at a MOI of 5, 10 and 20, respectively. 16 h p.i. the extent of apoptosis was analyzed using the Cell Death Detection ELISA kit (Roche Diagnostics, Mannheim) according to the manufacture's instructions. Briefly, 16 h p.i. medium was removed and cells were incubated in lysis buffer. After lysis, intact nuclei were pelleted by centrifugation and aliquots of supernatant were transferred to streptavidin-coated wells of microtiter plates. The amount of apoptoic nuclesomes present in the sample was determined using mouse monoclonal antibodies directed against DNA and histones, and spectrophotometrical analysis.

Propidium iodide staining. To determine nuclear fragmentation, monolayers of $1 \times 10^6$ confluent CEF grown in 6-well tissue-culture plates were infected with MVA, MVA-$_\Delta$E3L and MVA-E3rev at an MOI of 5IU and 20IU. Ninety minutes after infection at 4° C. cells were washed twice with MEM containing 10% lactalbumin and 5% BMS. At various time points post infection cells were trypsinized, collected and stored in 70% ethanol at 4° C. On the following day, cells were washed twice in PBS and resuspended in PBS containing propidium iodide with a final concentration of 50 µg/ml. Samples were stored for 1 h at 4° C. in the dark and analyzed with a Becton Dickinson FACScalibur apparatus as described previously (Nicoletti, I.; Migliorati, G.; Pagliacci, M. C.; Grignani, F. and Riccardi, C. (1991). A rapid and simple method for measuring thymocyte apoptosis by propidium staining and flow cytometry. J. Immunol. Methods 139: 271–279).

3. Generation of Recombinant MVA Viruses 3.1. Construction of Vector Plasmids

To allow the generation of recombinant MVA using E3L based selection novel vector plasmids were constructed on the basis of pIII plasmid vectors which contain MVA flanking sequences (flank III-1 and flank III-2) to target insertion of recombinant DNA precisely to the site of the naturally occuring deletion III within the MVA genome (Sutter & Moss 1992, Staib et al. 2000). To generate the plasmid vector pIII-E3-$P_{sH5}$ a 627 bp DNA fragment containing the complete coding sequence of the MVA E3L gene under transcriptional control of its authentic promoter sequence was prepared by PCR, treated with Klenow and inserted between the flank III-1 and flank III-2 DNA sequences in plasmid pLW9 via the restriction site BamHI (Wyatt, L. et al. 1996, Vaccine 14: 1451–1458). A 723-bp DNA fragment containing the $_{gfp}$ open reading frame was excised from pEGFP-N1 (CLONETECH Laboratories GmbH, Heidelberg, Germany) using the restriction endonucleases BamHI and NotI, treated with Klenow polymerase, and inserted into the restriction site SmaI of pIII-E3-$P_{sH5}$ to obtain pIII-E3-$P_{sH5}$-gfp.

3.2. Formation and Isolation of Recombinant MVA-PsH5-gfp

Monolayers of $1 \times 10^6$ confluent BHK-21 cells grown in 6-well tissue-culture plates (Costar, Corning N.Y., USA) were infected with MVA-$_\Delta$E3L at a multiplicity of infection (MOI) of 0.01 IU per cell. Ninety min after infection cells were transfected with 10 µg of pIII-E3-$P_{sH5}$-gfp DNA per well using calcium phosphate (CellPhect Transfection Kit, Amersham Pharmacia Biotech, Freiburg, Germany) as recommended by the manufacturer. Forty-eight h after infection the cells were harvested, freeze-thawed three times, and homogenized in a cup sonicator (Sonopuls HD 200, Bandelin, Germany). Ten-fold serial dilutions ($10^{-1}$ to $10^{-4}$) of the harvested material in medium were used to infect subconfluent monolayers of CEF cells grown in 6-well tissue-culture plates. After three days incubation at 37° C. foci of CEF cells infected with recombinant UVA were monitored for GFP synthesis and picked in a 20 µl volume by aspiration with an air-displacement pipette, transferred to microcentrifuge tubes containing 500 µl medium, and processed by freeze-thawing and sonication for another infection of CEF cell monolayers. After three consecutive rounds of plaque purification in CEF cells the recombinant MVA-PsH5-gfp viruses were amplified by infection of CEF monolayers, and the DNA was analyzed by PCR to confirm genetic homogenity of the virus stock.

Results

Generation of Mutant Virus MVA-$_\Delta$E3L

To evaluate the relevance of the key interferon-resistance gene E3L in the MVA life cycle, we used homologous recombination to replace the complete promoter and coding sequences of the E3L open reading frame in the MVA genome with a vaccinia virus K1L gene expression cassette (FIG. 1A). This marker allows for stringent growth selection of mutated viruses upon infection of rabbit kidney RK-13 cells, in a second step using nonselective growth conditions it is simply removed again by further homologous recombination between flanking repetitive DNA sequences (Staib et al., 2000). Recombinant MVA with deleted E3L gene sequences were isolated during several rounds of plaque purification on RK-13 and BHK-21 cell monolayers. During plaque cloning the expected genome alterations were monitored by PCR (FIG. 1B). Primary virus stocks were amplified on BHK-21 cells, re-assessed by Southern blot analysis of viral DNA (FIG. 1C), and designated MVA-$_\Delta$E3L. Western blotting of cell lysates which were prepared in the presence or absence of arabinoside C confirmed the synthesis of E3L protein in cells infected with wild-type MVA, whereas no E3L polypeptides could be detected after infection with MVA-$_\Delta$E3L (FIG. 1D).

Replication of MVA-$_\Delta$E3L is Inhibited in CEF

In the attempt to generate secondary virus stocks of MVA-$_\Delta$E3L we infected confluent CEF monolayers at low multiplicity of infection (MOI), but to our surprise the virus failed to amplify. Suspecting a host range phenotype, we wished to comparatively analyze virus growth after infection of BHK-21 and CEF cells. A growth deficiency could result from a defect in virus replication or virus spread. First, we determined virus yields in multiple-step growth experiments infecting cells with MVA or MVA-$_\Delta$E3L at 0.1 infectious units (IU) per cell (FIG. 2A, 2B). At this multiplicity, replication and spread of MVA and MVA-$_\Delta$E3L in BHK-21 cells were close to identical with very similar peaks of infectivity titers reached between 20 and 48 h after infection (FIG. 2A). As expected MVA replicated efficiently in CEF. In contrast, titers of MVA-$_\Delta$E3L in CEF steadily decreased in comparison to input infectivity suggesting a virtual absence of productive virus growth (FIG. 2B). In addition, we analyzed one-step virus growth using a MOI of 10 for infection, and again we found equal capabilties of MVA and MVA-$_\Delta$E3L to multiply in BHK-21 cells. Paralleling the data from multiple-step-growth analysis, infectivity titers of MVA-$_\Delta$E3L detected in CEF after 8, 22, or 48 h of infection never reached the level of infectivity found after virus adsorption (FIG. 2C, FIG. 2D). We concluded from these experiments that MVA-$_\Delta$E3L has a specific replication defect in CEF. To verify that this host range phenotype is solely due to the deletion of the E3L gene sequences we reinserted the E3L gene under transcriptional control of its authentic promoter sequence into the genome of MVA-$_\Delta$E3L to generate the revertant virus MVA-E3rev. Briefly, we used the plasmid vector pE3Lrev containing a DNA fragment comprising the complete E3L gene expression cassette together with its genomic flanking sequences for transfection of MVA-$_\Delta$E3L-infected BHK cells. Revertant virus MVA-E3rev could be readily isolated by plaque purification in CEF monolayers. Stable reinsertion of E3L was confirmed by PCR with genomic MVA-E3rev DNA, and Western blot analysis of cell lysates revealed synthesis of E3L protein at levels equal to wild-type MVA (data not shown). Already the fact that MVA-E3rev could be isolated without need for additional screening or selection suggested a successful reversion of the growth defect of MVA-$_\Delta$E3L in CEF. Correspondingly, upon multiple-step and one-step growth analysis of MVA-E3rev in both BHK-21 and CEF cells we found levels of virus replication similar to wild-type MVA (FIGS. 2A-D). From this data we concluded that E3L function is necessary to maintain MVA replication in CEF, the cell culture system in which the virus had been developed upon longterm passage.

Reduced Viral Protein and DNA Synthesis in CEF Infected With MVA-$_\Delta$E3L

Figure 3:
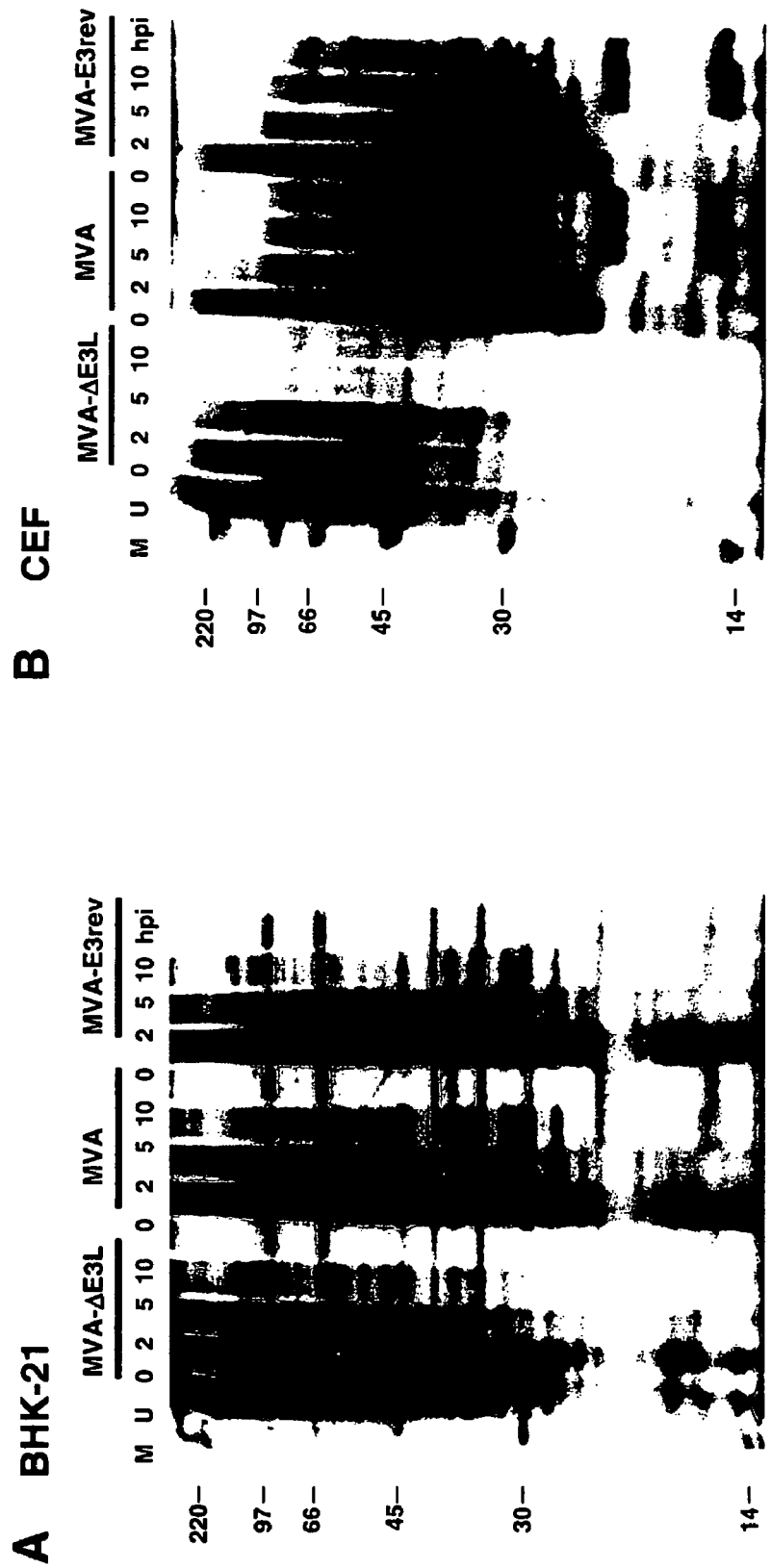

To better characterize the non-permissive infection of CEF with MVA-$_\Delta$E3L, we sought to determine wether the failure to produce infectious viral progeny resulted from reduced viral protein synthesis. CEF and BHK cells were metabolically labeled with [$^{35}$S]methionine at various times after infection with MVA, MVA-$_\Delta$E3L, or MVA-E3rev. After each labeling period, lysates were prepared and analyzed by SDS-PAGE and autoradiography. In BHK cells infected with MVA, late viral protein synthesis occurred at 5 h after infection and became prominent with profound shut-off of cell protein synthesis at 10 h after infection (FIG. 3A). Similar patterns of viral proteins were found in BHK cells infected with MVA-$_\Delta$E3L or MVA-E3rev (FIG. 3A). In CEF infected with MVA or MVA-E3rev abundant late viral protein synthesis was found at times 5 h and 10 h after infection (FIG. 3B). By contrast, in CEF cells infected with MVA-$_\Delta$E3L we could hardly detect polypeptide bands specific for viral protein production (FIG. 3B). Some weak bands of polypeptides co-migrating with typical late viral proteins became visible with the prominent shut-off of host cell protein synthesis at times after 5 h of infection.

Because synthesis of the abundant viral late proteins is dependent on the replication of viral DNA, we further examined this step in the life cycle of MVA-$_\Delta$E3L comparing infection of BHK-21 and CEF cells. Viral DNA synthesis was monitored by isolating total DNA from infected cells at different times during a one-step infection and transferring this DNA onto a membrane which was hybridized with a radioactively labeled MVA-DNA probe (FIG. 3C, D). As shown by FIG. 3C, in BHK-21 cells infected with MVA-$_\Delta$E3L or MVA the accumulation of viral DNA occured with very similar kinetics and quantities. Also in CEF cells we found viral DNA being increasingly made after infection with both viruses (FIG. 3D). In the case of the non-permissve CEF infection with MVA-$_\Delta$E3L, however, we detected, compared to permissive conditions, lesser amounts of DNA at time points 6 h and 12 h after infection. Thus the drastically diminished protein synthesis found in MVA-$_\Delta$E3L-infected CEF was not correlated with a gross block of virus-specifc DNA replication, while production of viral DNA appeared arrested at later times during non-permissive infection.

Induction of Apoptosis in CEF Infected With MVA-$_\Delta$E3L

Figure 4:
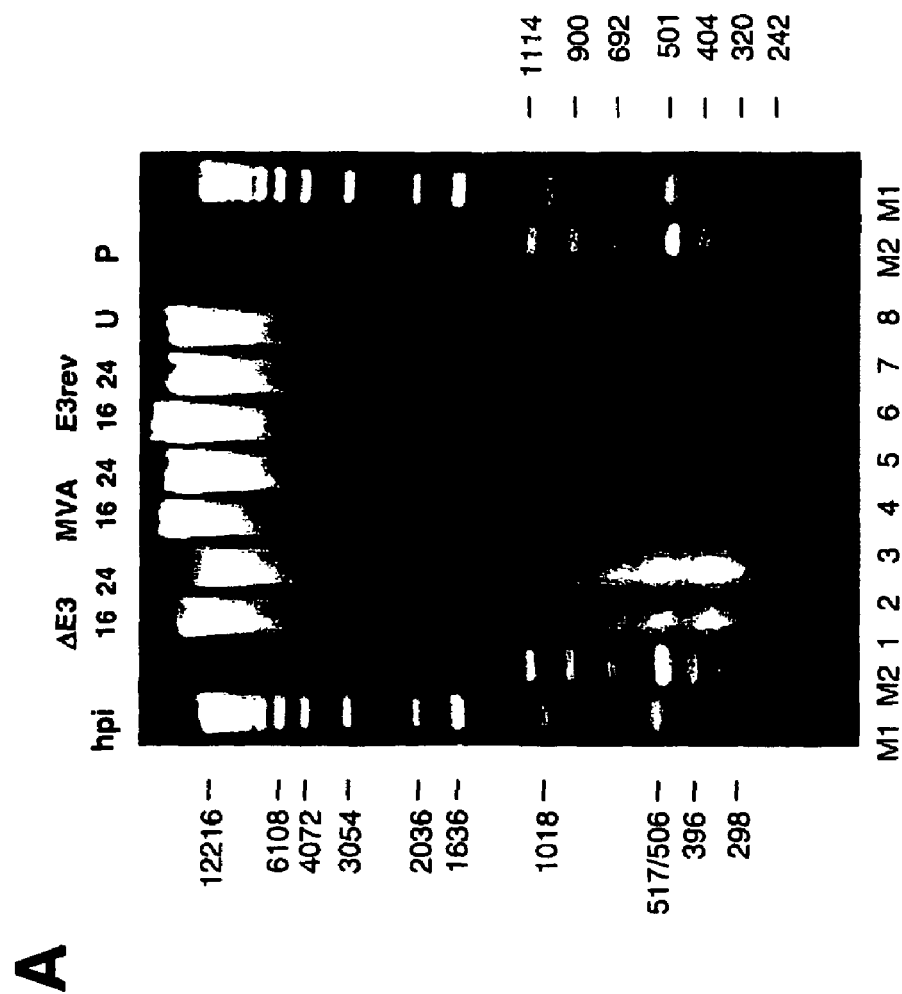

This infection phenotype being characterized by prominent shutdown of viral protein synthesis together with maintained capacity for viral DNA replication was reminiscent of the non-permissive vaccinia virus infection of Chinese hamster ovary (CHO) cells (Spehner et al., 1988; Ramsey-Ewing and Moss, 1995). The abortive vaccinia virus-CHO infection is associated with induction of apoptosis that can be overcome by co-expression of the cowpox virus gene CHO$_{hr}$ (Ink et al., 1995, Ramsey-Ewing and Moss, 1998). Furthermore, also the vaccinia E3L gene product was described to inhibit induction of apoptosis in vaccinia virus-infected HeLa cells (Lee and Esteban, 1994; Kibler et al., 1997). Because we had observed an unusual cell shrinkage when monitoring CEF cultures by light microscopy within 24 h of infection with MVA-$_\Delta$E3L, it appeared important to probe if the growth restriction of MVA-$_\Delta$E3L in CEF cells could be possibly linked to apoptosis. In a first standard assay for apoptosis we monitored for the characteristic cleavage of DNA into 180 bp-multimers corresponding to a nucleosomal "DNA ladder" (Wyllie et al., 1980). Total cellular DNA was isolated from CEF cultures infected either with MVA-$_\Delta$E3L, MVA or MVA-E3rev, separated by agarose gel electrophoresis, and visualized upon ethidium bromide staining. We observed the typical fragmentations of cellular DNA indicative for apoptosis in samples from CEF cells infected with MVA-$_\Delta$E3L for 16 h and 24 h. In contrast, no such DNA laddering was detectable in samples from CEF cells infected with MVA or revertant virus MVA-E3rev (FIG. 4A). Another hallmark for apoptosis is the appearance of extranuclear nucleosomes. Therefore, we stained CEF cultures with Hoechst 3343 and screened for apoptotic bodies in individual cells. At 16 h after infection with MVA-$_\Delta$E3L we could easily detect cytoplasmic vacuoles that stained extensively with Hoechst 3343 (FIG. 4B). In addition, this assay allowed to quantify the number of apoptotic cells by determining the percentage of cells with extranuclear staining in randomly selected areas with 300 to 500 cells (in triplicate, FIG. 4C). After infection with MVA-$_\Delta$E3L, we found clear signs of apoptosis in about 20% of all cells when using a multiplicity of 5

IU/cell. In experiments done at a multiplicity of 20 IU/cell the percentage of apoptotic cells increased to about 30%. In contrast, at the most 4% of cells infected with wild-type MVA or revertant virus MVA-$_\Delta$E3rev, and only 1% of mock-infected cells were counted positive for extranuclear staining. To demonstrate that this apoptotic process does not only occur on a DNA level, we also investigated intracellular proteolysis by caspases using the specific peptide substrate Asp-Glu-Val-Asp (DEVD) (Salvesen and Dixit, 1997). Using an established fluorescence assay DEVD-cleaving activity was measured in cell extracts prepared from CEF at 16 h after infection (Linsinger et al. 1999). Again after infection with MVA-$_\Delta$E3L we found strongly enhanced DEVD-cleavage activities, while extracts from MVA or MVA-E3rev infected cells contained little if any detectable activity (FIG. 4D). These results clearly demonstrated that the growth defect of MVA-$_\Delta$E3L in CEF was associated with an induction of apoptosis.

Furthermore, we wished to assess wether the onset of apoptosis in MVA-$_\Delta$E3L-infected CEF could be more obviously linked to the host range restriction phenotype. Although our previous experiments were done a multiplicity of 20 IU/cell, which should guarantee an infection of all the cells, only approximately 30% of the cells were scored apoptotic upon Hoechst staining. Therefore, first, we were interested to more carefully titrate MVA-$_\Delta$E3L with regard to the extent of apoptosis. We infected CEF cells with 1, 5, 10 or 20 IU MVA-$_\Delta$E3L, MVA, or MVA-E3rev, and at 16 h after infection we quantified apoptosis using an ELISA based on the specific detection of apoptotic nucleosomes with mouse monoclonal antibodies (Cell Death Detection ELISA Kit, Roche Diagnostics, Mannheim) (FIG. 5A). We found clear evidence for apoptosis in CEF inoculated with the lowest dose of 1 IU MVA-$_\Delta$E3L per cell. Levels of apoptosis steadily augmented with increasing amounts of MVA-$_\Delta$E3L used for infection, while even higher dose infections with MVA or MVA-E3rev resulted in amounts of cell death that barely exceeded background levels. The accuracy of an enumeration of apoptotic cells following Hoechst staining could have been limited by the fact that a fraction of apoptotic cells is likely to be lost for analysis due to detachment during handling of infected cell monolayers. To use an alternative protocol for analyzing the percentage of dead cells present after infection with an MOI of 20, we stained apoptotic nuclei with propidium iodide and counted them by flow cytometry at various time points (Nicoletti et al., 1991). As early as 6 h after infection with MVA-$_\Delta$E3L we detected an increased number of apoptotic nuclei in comparison to CEF infected with MVA or MVA-E3rev (FIG. 5B). At following time points the percentage of dead cells in MVA-$_\Delta$E3L-infected CEF raised continuously accounting for about 70% of all the cells at 24 h post infection. This data suggested that extent and kinetics of apoptosis found in MVA-$_\Delta$E3L-infected CEF correlated with the growth restriction phenotype being characterized by reduced protein and DNA synthesis.

Induction of IFN Type I in CEF Infected With MVA-$_\Delta$E3L

Figure 6:
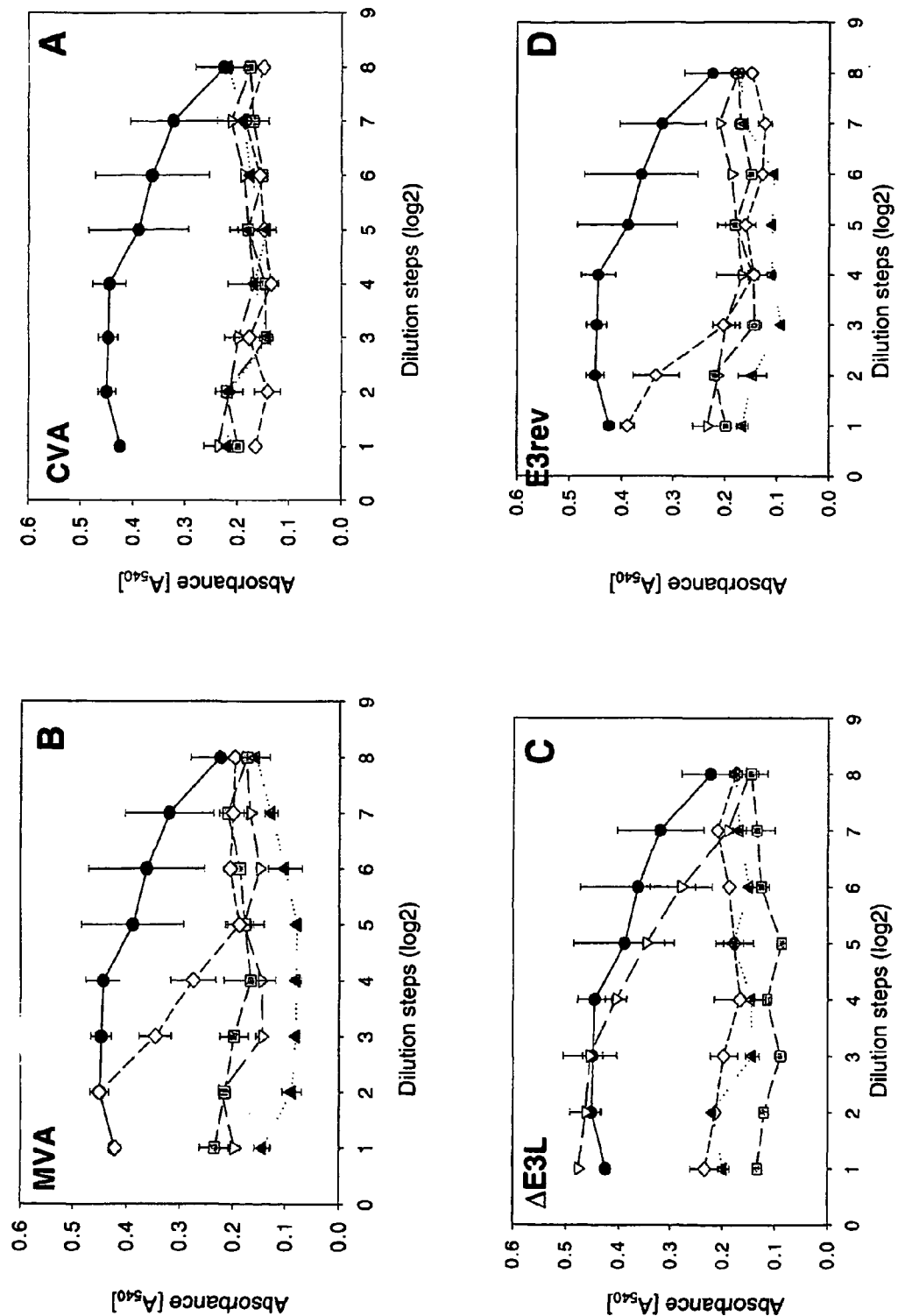

Induction of apoptosis in HeLa cells by vaccinia virus WR with E3L deleted has been linked to the function of E3L as potent dsRNA-binding protein which interferes with the activation of the principal IFN-regulated antiviral enzymes PKR and RNase L (Lee and Esteban, 1994; Kibler et al. 1997). Another characteristic feature of this vaccinia virus mutant is its increased sensitivity to IFN treatment (Beattie et al. 1991; Beattie et al., 1995). Interestingly, deletion of E3L function upon vaccinia virus Copenhagen infection also results in the induction of IFN-β synthesis through activation of interferon regulatory factor 3 (IRF-3). Therefore, we wished to comparatively monitor for the presence of IFN after infection of CEF with MVA-$_\Delta$E3L. We inoculated CEF monolayers grown in 6-well tissue culture plates with 10 IU/cell of MVA-$_\Delta$E3L, MVA, MVA-E3rev, wild-type vaccinia viruses CVA, or WR. Cell-free supernatants were collected at 24 h after infection and tested for activities of chicken IFN type I in comparison to recombinant chicken IFN (recIFN, 250 U/ml) using an established assay (FIG. 6). Supernatants from cells infected with wild-type vaccinia virus CVA contained no detectable IFN activity (FIG. 6A). The same result was obtained after infection with vaccinia virus WR (data not shown). In contrast, IFN activity was clearly present in medium from MVA infected CEF (FIG. 6B). Surprisingly, highest levels of IFN were found after infection with MVA-$_\Delta$E3L reaching activities similar to those obtained with recIFN used as control (FIG. 6C). Also after infection with MVA-E3rev we detected IFN activity albeit lower levels and very comparable to the activity found after infection with non-mutated MVA (FIG. 6D). This data demonstrated that already the permissive infection of CEF with MVA induced an accumulation of biologically active type I IFN, while the non-permissive MVA-$_\Delta$E3L infection produced even more IFN.

Effect of IFN Treatment on Vaccinia Virus Infection in CEF

Figure 7:
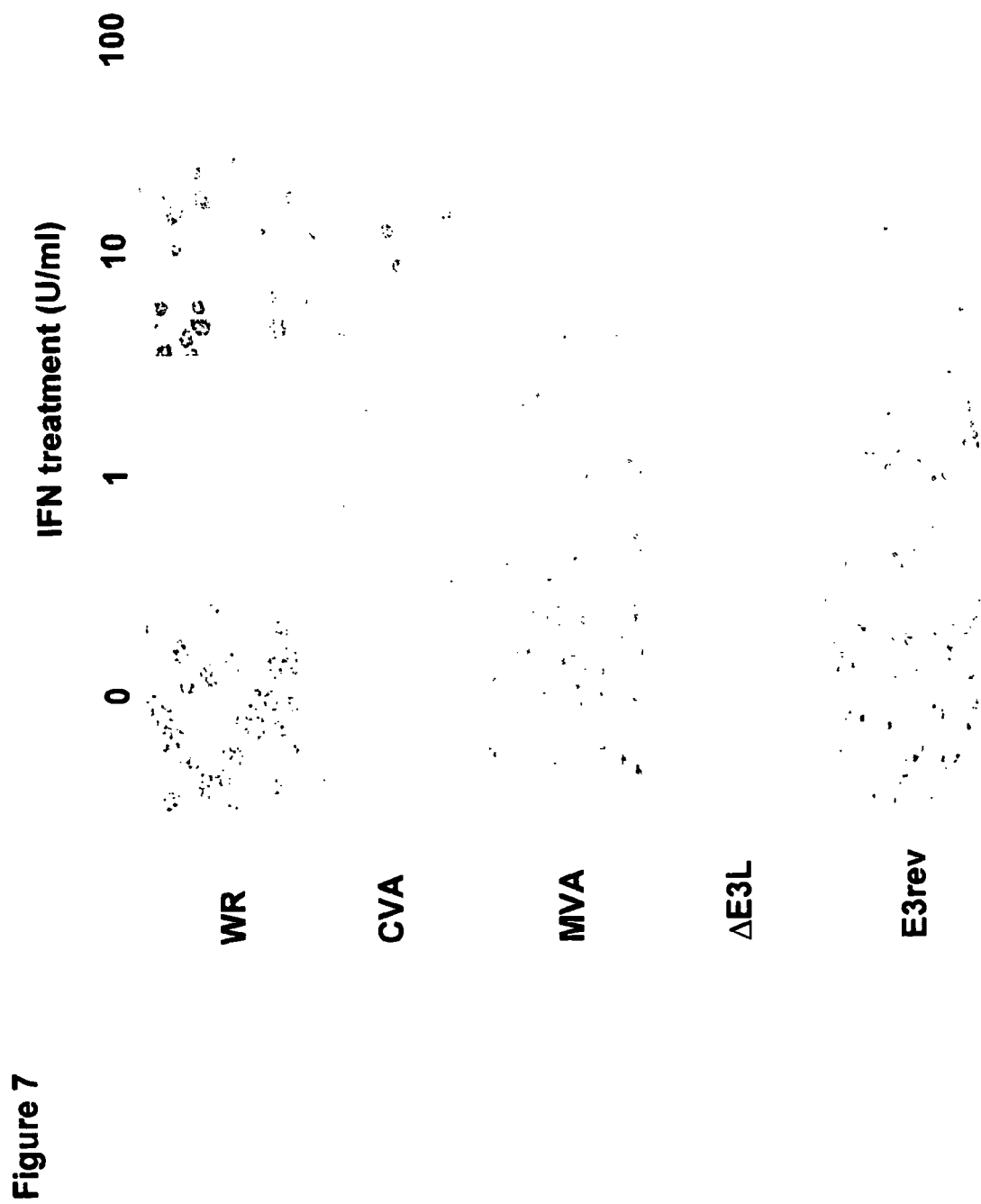
Figure 8:
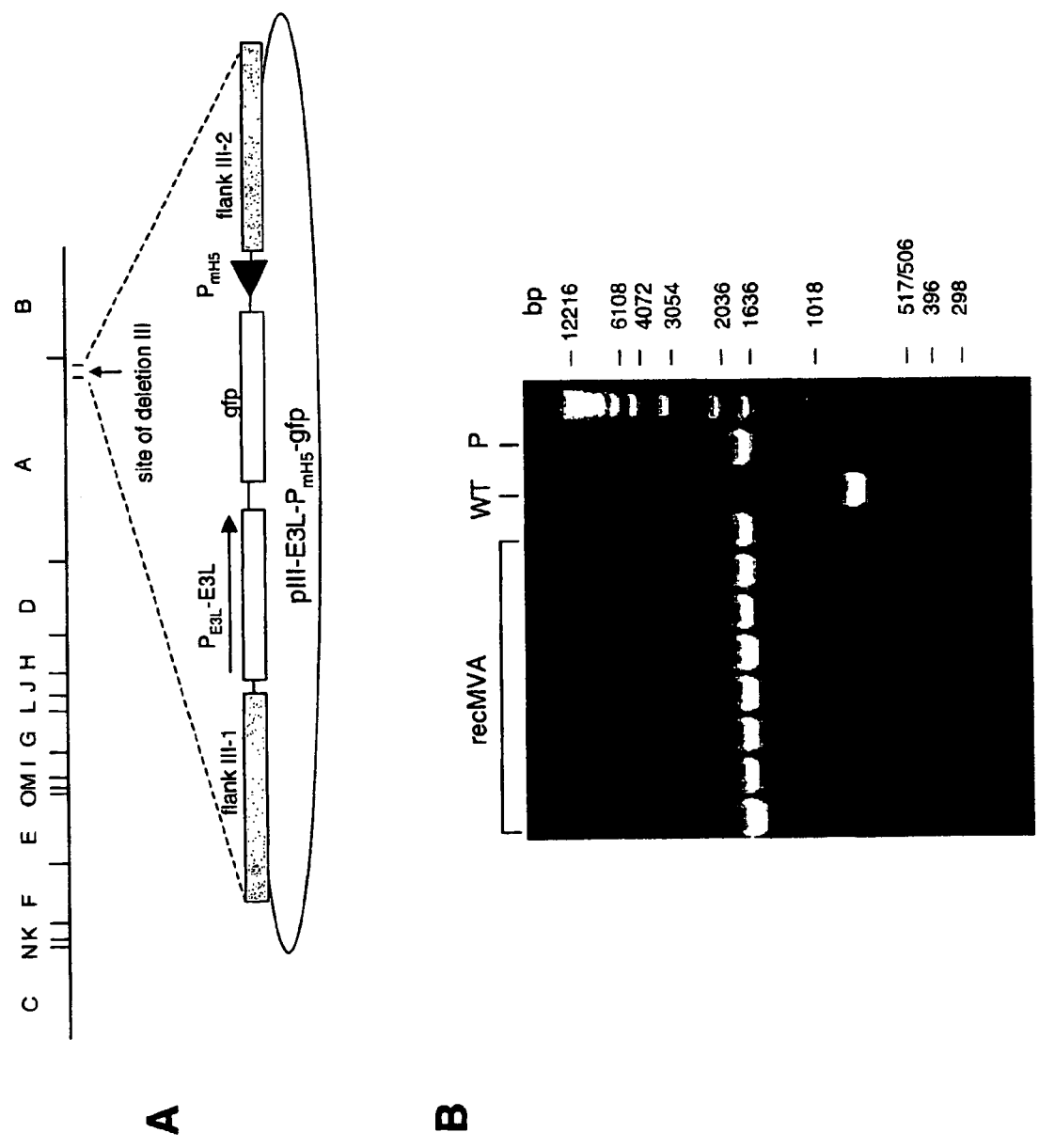

Upon infection of mammalian cells vaccinia virus replication has been found to be relatively resistant to IFN activity. Interestingly, this appears to be different in CEF cultures in which pretreatment with chicken interferon can inhibit vaccinia virus growth. To determine the effect of IFN on MVA infection, we pre-treated CEF monolayers with increasing amounts of recombinant chicken IFN type I for 24 h, before infecting the cultures at low MOI with MVA, MVA-$_\Delta$E3L, or MVA-E3rev, or for comparison with vaccinia viruses CVA or WR. At 48 h after infection cell monolayers were fixed and foci of virus infected cells were visualized using vaccinia virus-specific immunostaining (FIG. 7). After infection with vaccinia viruses WR or CVA, we revealed multiple virus plaques that had formed in monolayers being mock treated or treated with low amounts of IFN (1 or 10 U IFN/ml medium). Yet, the presence of 10 U IFN/ml medium resulted in less virus plaques of usually smaller size. No more plaque formation was detectable in monolayers preincubated with 100 U IFN/ml medium or 1000 U IFN/ml medium (data not shown). Immunostaining of MVA infected CEF revealed foci of virus-positive cells which remained associated with the cell monolayer demonstrating the typical lower cytopathogenicity of MVA infection. Despite of this difference in plaque phenotype, formation of MVA-infected cell foci upon IFN treatment was very comparable to plaque formation seen with vaccinia virus WR or CVA. We found MVA-infected cells in monolayers treated with up to 10 U IFN/ml medium. This latter amount clearly affected number and size of the foci, while higher IFN concentrations resulted in complete growth inhibition. In sharp contrast, there were no detectable virus-infected cells in monolayers that were inoculated with MVA-$_\Delta$E3L irrespective of IFN treatment confirming the incapability of this mutant to productively replicate in CEF. Whereas upon infection with MVA-E3rev we found again a foci formation that was identical to the pattern established with wild-type MVA. This data confirmed earlier work that suggested a relative IFN sensitivity of vaccinia virus infection in CEF, and additionally demonstrated that the IFN-mediated inhibition of CEF-adapted MVA is very comparable to the IFN effect found upon infection with vaccinia virus strains WR and CVA.

Generation of Recombinant MVA by Restoration of E3L Function

Single gene dependent host range phenotypes in vaccinia virus infection can be elegantly used for efficient selection of recombinant viruses through reinsertion of the host range gene into the mutant virus genome. To verify if the growth restriction of MVA-$_\Delta$E3L in CEF would allow for such host range selection we constructed an MVA insertion plasmid to target reintroduction of the E3L coding sequences under transcriptional control of its authentic promoter into the site of deletion III in the MVA genome. The addition of an expression cassette of the A. victoriae gfp gene that served as a model recombinant gene being expressed with the vaccinia virus-specific promoter PmH5 resulted in the MVA vector plasmid pIII-E3L-P$_{HS}$-gfp (FIG. 7A). After transfection of this plasmid into MVA-$_\Delta$E3L infected BHK-21 cells we observed a few gfp gene expressing cell clusters among the many cells showing virus-specific cytopathic effects which suggested that recombinant MVA had formed. To test for a selective restoration of virus growth on CEF we inoculated ten-fold dilutions of the virus material obtained following transfection on CEF monolayers grown in 6-well tissue culture plates. After three days we observed the formation of virus plaques which virtually all contained GFP producing cells. From ten well separated plaques being processed for further amplification on CEF, we recovered eight different isolates of recombinant MVA-P$_{HS}$-GFP after one additional passage. PCR analysis of viral DNA demonstrated that all virus isolates represented bona fide recombinants carrying stable insertions at the site of deletion III within their genomes (FIG. 7B). The ease with which these virus isolates were obtained reflects the essential requirement of E3L function for MVA growth on CEF, and suggests that the E3L-specific rescue of MVA-$_\Delta$E3L can be proposed as efficient host range selection protocol to generate recombinant MVA.

REFERENCES

Bair, C. H., Chung, C. S., Vasilevskaya, I. A. and Chang, W. (1996). Isolation and characterization of a Chinese hamster ovary mutant cell line with altered sensitivity to vaccinia virus killing. J. Virol. 70: 4655–4666

Beattie, E., Denzler, K., Taraglia, J., Paoletti, E. and B. L. Jacobs (1995). Reversal of the interferon-snsitive phenotype of an E3L-minus vaccinia virus by expression of the reovirus S4 gene. J. Virol. 69, 499–505.

Chang, H.-W., Uribe, L. H. and Jacobs, B. L. (1995). Rescue of vaccinia virus lacking the E3L gene by mutants of E3L. J. Virol. 69, 6605–6608.)

Beattie, E., Kaufman, E., Martinez, H., Perkus, M., Jacobs, B. L., Paoletti, E. and J. Tartaglia. (1996). Host-range restriction of vaccinia virus E3L-specific deletion mutants. Virus Genes 12:89–94.

Lee, S. B. and Esteban, M. (1994). The interferon-induced double-stranded RNA-activated protein kinase induces apoptosis. Virology 199: 491–496.

Nicoletti, I., Migliorati, G., Pagliacci, M. C., Grignani, F. and Riccardi, C. (1991). A rapid and simple method for measuring thymocyte apoptosis by propidium iodide staining and flow cytometry. J. Immunol. Methods 139, 271–279

Salvesen, G. S. and V. M. Dixit 1997. Caspases: intracellular signalling by proteolysis. Cell 91:443–446. Linsinger, G.; Wilhelm, S.; Wagner, H.; Hacker, G. (1999). Uncouplers of oxidative phosphorylation can enhance a Fas death signal. Mol. Cell. Biol., 19(5), 3299–3311.

Wyllie, A. H., Kerr, J. F. R. and Currie, A. R. Int. Rev. Cyto. 68, 251–306 (1980)

What is claimed is:

1. MVA-knock-out-mutant, wherein the MVA ORF 050L gene or a functional part thereof has been inactivated in the viral genome.

2. MVA-knock-out-mutant of claim 1, in which the MVA ORF 050L gene or a functional part thereof has been inactivated by deletion from the viral genome.

3. An isolated host cell, wherein the cell has been infected with the MVA of claim 1.

4. The isolated host cell of claim 3, which is a eucaryotic cell.

5. The isolated host cell of claim 4, which is a BHK-21 cell, a BS-C-1 cell, a MA104 cell, or a CV-1 cell.

6. A method for generating a recombinant MVA, the method comprising:
   (a) infecting a host cell with an MVA, wherein an MVA ORF 050L gene or a functional part thereof has been inactivated in the MVA;
   (b) transfecting the host cell with a DNA-vector construct comprising an MVA ORF 050L gene or encoding a functionally equivalent MVA ORF 050L derived polypeptide; and
   (c) selecting restored MVA by growth on CEF cells or chicken embryo derived LSCC-H32 cells or avian cells, thereby generating a recombinant MVA.

7. The method of claim 6, wherein the DNA-vector construct further comprises a nucleic acid sequence encoding a foreign protein.

8. The method of claim 7, wherein the foreign protein is a heterologous protein selected from the group consisting of a therapeutic polypeptide, an antigen encoded by a pathogenic agent, and an immunogenic fragment of said antigen.

9. The method of claim 8, wherein the therapeutic polypeptide is selected from the group consisting of t-PA and interferon.

10. The method of claim 8, wherein the pathogenic agent is selected from the group consisting of a virus, a bacterium, a protozoan, a parasite, and a tumor cell.

11. The method of claim 10, wherein the virus is selected from the group consisting of an influenza virus, a measles virus, a respiratory syncytial virus, a dengue virus, a human immunodeficiency virus, a human hepatitis virus, a herpes virus, and a papilloma virus.

12. The method of claim 10, wherein the protozoan is Plasmodium falciparum.

13. The method of claim 10, wherein the bacterium is a tuberculosis-causing Mycobacterium.

14. The method of claim 8, wherein the foreign protein is a tumor-associated antigen or immunogenic fragment thereof, selected from the group consisting of a melanoma-associated differentiation antigen, a cancer-testes antigen, and a non-mutated shared antigen overexpressed in a tumor.

15. The method of claim 14, wherein the melanoma-associated differentiation antigen is selected from the group consisting of a tyrosinase, a tyrosinase-related protein 1, and a tyrosinase-related protein 2.

16. The method of claim 14, wherein the cancer-testes antigen is selected from the group consisting of MAGE-1, MAGE-2, MAGE-3 and BAGE.

17. The method of claim 14, wherein the non-mutated shared antigen overexpressed in a tumor is selected from the group consisting of Her-2/neu, MUC -1, and p53.

18. The method of claim 7, wherein the MVA ORF 050L gene and the nucleic acid sequence encoding the foreign protein are both flanked by a DNA sequence flanking a non-essential site within an MVA genome.

19. The method of claim 18, wherein one or both of the MVA ORF 050L gene and the nucleic acid sequence encoding the foreign protein is flanked by a site of deletion III in an MVA genome.

20. The method of claim 6, wherein the DNA vector construct comprises a plasmid.

21. The method of claim 6, wherein the avian cell is selected from the group consisting of a quail QT6 fibroblast and a quail QT35 fibroblast.

22. The method of claim 6, wherein the isolated host cell is a eucaryotic cell.

23. The method of claim 22, wherein the isolated host cell is selected from the group consisting of a BHK-21 cell, a BS-C-1 cell, a MA104 cell, and a CV-1 cell.

* * * * *